US007205451B2

(12) United States Patent
Haring et al.

(10) Patent No.: US 7,205,451 B2
(45) Date of Patent: Apr. 17, 2007

(54) NUCLEOTIDE SEQUENCES CODING SIGNAL TRANSDUCTION COMPONENTS IN DURABLE AND BROAD-RANGE RESISTANCE STRATEGIES BASED ON PLANT DEFENCE

(75) Inventors: Michel Haring, Rl Haarlem (NL); Augustinus Franciscus Maria Simons, Jl Ede (NL); Jacobus Hubertus Vossen, Ea Amsterdam (NL); Bernardus Johannes Clemens Cornelissen, Eb Warmond (NL)

(73) Assignee: Keygene N.V., Wageningen (NL)

( * ) Notice: Subject to any disclaimer, the term of this patent is extended or adjusted under 35 U.S.C. 154(b) by 111 days.

(21) Appl. No.: 10/298,638

(22) Filed: Nov. 19, 2002

(65) Prior Publication Data
US 2003/0177527 A1 Sep. 18, 2003

Related U.S. Application Data

(63) Continuation of application No. PCT/EP01/06458, filed on May 18, 2001.

(30) Foreign Application Priority Data
May 19, 2000 (EP) .................................. 00401402

(51) Int. Cl.
C12N 15/29 (2006.01)
C12N 15/82 (2006.01)
A01H 5/00 (2006.01)
(52) U.S. Cl. ...................... 800/279; 800/278; 800/298; 435/320.1; 435/468; 435/419; 536/23.6
(58) Field of Classification Search ................. 800/278, 800/279, 298, 295; 435/468, 320.1; 536/23.1, 536/23.6, 24.5
See application file for complete search history.

(56) References Cited

U.S. PATENT DOCUMENTS 5,304,490 A * 4/1994 Bird et al. ................ 435/320.1
5,986,082 A * 11/1999 Uknes et al. ................ 800/279

FOREIGN PATENT DOCUMENTS

| EP | 1033405 A2 | 9/2000 |
| WO | WO 92/03562 A1 | 3/1992 |
| WO | WO 96/32007 A1 | 10/1996 |
| WO | WO 97/06259 A2 | 2/1997 |

OTHER PUBLICATIONS

Database GENEBL, May 12, 1998, Nakamura, Y.: "Arabidopsis thalina genomic DNA, chromosome 5, TAC clone: K919", XP002150176.
Database GENEMBL, Aug. 24, 1998, Nakamura, Y.: "Arabidopsis thaliana genomic DNA chromosme 5, P1 clone: MRB17", XP002150177.
Database GENEMBL, Apr. 7, 2000, Alcala et al.: "EST329156 tomato germinating seedlings, TAMU Lycopersicon esculentum cDNA clone cLEIL3H22 5', mRNA sequence", XP002150174.
Database GENEMBL, Nov. 14, 1997, Horvath et al.: "Arabidopsis thaliana protein phosphatase U (PPU) mRNA, partial cds", XP002150175.
(Abstract) Fray et al., "Nucleotide sequence of a heat-shock and ripening-related complementary DNA from tomato", Nucleic Acid Research, vol. 18, No. 23, 1990, p. 7148.
Database GENEMBL, Feb. 20, 1998, Ganal, et al.: "CD40 .complete tomato leaf cDNA from cv. LA0490 Lycopersicon esculentum cDNA clone CD40, mRNA sequence", XP002150167.
Database GENEMBL, Mar. 6, 2000, Kaneko et al.: "Arabidopsis thaliana genomic DNA, chromosome 3, TAC clone: K24A2", XP002150168.
Database GENEMBL, Jan. 31, 2000, Sasaki et al.: "Oryza sativa genomic DNA, chromosome 1, clone:P0499C11", XP02150169.
Database GENEMBL, May 17, 1999, Vlachonasios et al.: "Lycopersicon esculentum 17.7 kD class I small heat shock protein (HSP17.7) mRNA, complete cds", XP002150170.
Database GENEMBL, May 17, 1999, Vlachonasios et al.: "Lycopersicon esculentum 17.8 kD class I small heat shock protein (HSP17.8) mRNA, complete cds", XP002150171.
Database GENEMBL, May 17, 1999, Vlachonasios et al.: "Lycopersicon esculentum 17.6 kD class I small heat shock protein (HSP17.6) mRNA, complete cds", XP002150172.
Database GENEMBL, Dec. 5, 1990, Fray et al.: "Lycopersicon esculentum for small heat-shock protein (class I)", XP002150173.
Kadyrzhanova et al.: "Molecular cloning of a novel heat induced/chilling tolerance related cDNA in tomato fruit by use of mRNA differential display", Plant Molecular Biology, vol. 36, No. 6, Apr. 1998, pp. 885-895.
Zhou et al.: "The Pto kinase conferring resistance to tomato bacterial speck disease interacts with proteins that bind a cis-element of pathogenesis-related genes", The EMBO Journal, vol. 16, No. 11, 1997, pp. 3207-3218.

(Continued)

Primary Examiner—Medina A. Ibrahim
(74) Attorney, Agent, or Firm—Birch, Stewart, Kolasch & Birch, LLP

(57) ABSTRACT

Nucleotide sequences coding signal transduction components in durable and broad-range resistance strategies based on plant defense. The invention relates to nucleotide sequences derived from a plant genome, capable of encoding a polypeptide product which can be activated as a signaling molecule in the signal transduction pathway of resistance to a plant pathogen which resistance results from the interaction between polypeptide products encoded by a resistance gene and elicitors encoded by an avirulence gene in said soil pant pathogen wherein the polypeptide product encoded by the nucleotide sequence interacts with a polypeplide product encoded by said resistance gene. The invention further relates to the use of these sequences and/or polypeptide products in the establishment of durable and broad range resistance strategies based on plant defense.

18 Claims, 17 Drawing Sheets

OTHER PUBLICATIONS

Zhou et al.: "The Tomato Gene Ptil Encodes a Serine/Threonine Kinase That is Phosphorylated by Pto and is Involved in that Hypersensitive Response", Cell, vol. 83, Dec. 15, 1995, pp. 925-935.

Aarts et al.: "Different requirements for EDS1 and NDR1 by disease resistance genes define at least two R gene-mediated signaling pathways in Arabidopsis", Proc. Natl. Acad. Sci., vol. 95, Aug. 1998, pp. 10306-10311.

Beffa et al.: "Cholera toxin elevates pathogen resistance and induces pathogenesis-related gene expression in tobacco", The EMBO Journal, vol. 14, No. 23, 1995, pp. 5753-5761.

Bourne et al.: "The GTPase superfamily: conserved structure and moleculr mechanism", Nature, vol. 349, Jan. 10, 1991, pp. 117-127.

Brunner at al.: "A Gain-of-Function Mutation in Drosophila MAP Kinase Activates Multiple Receptor Tyrosine Kinase Signaling Pathways", Cell, vol. 76, Mar. 11, 1994, pp. 875-888.

Claret et al.: A new group of conserved coactivators that increase the specificity of AP-1 transcription factors, Nature, vol. 383, Oct. 3, 1996, pp. 453-457.

Fields et al.: "A novel genetic system to detect protein—protein interactions", Nature, vol. 340, Jul. 20, 1989, pp. 245-246.

Grant et al.: "Structure of Arabidopsis RPM1 Gene Enabling Dual Specificity Disease Resistance", Science, vol. 269, Aug. 11, 1995, pp. 843-846.

Gyuris et al.: "Cdi1, a Human G1 and S Phase Protein Phosphatase That Associates with Cdk2", Cell, vol. 75, Nov. 19, 1993, pp. 791-803.

Maeda et al.: "Activation of Yeast PBS2 MAPKK by MAPKKKs or by Binding of SH3- Containing Osmosensor", Science, vol. 269, Jul. 28, 1995, pp. 554-558.

Ori et al.: "The I2C Family from the Wilt Disease Resistance Locus I2 Belongs to the Nucleotide Binding, Leucine-Rich Repeast Superfamily of Plant Resistance Genes", The Plant Cell, vol. 9, Apr. 1997, pp. 521-532.

Ramer et al.: "A dominant truncation of allele identifies a gene, STE20, that encodes a putative protein kinase necessary for mating in *Saccharomyces cervisiae*", Proc. Natl. Acad. Sci., vol. 90, Jan. 1993, pp. 452-456.

Simons et al.: "Dissection of the Fusarium I2 Gene Cluster in Tomato Reveals Six Homologs and One Active Gene Copy", The Plant Cell, vol. 10, Jun. 1998, pp. 1055-1068.

Song et al.: "A Receptor Kinase-Like Protein Encoded by the Rice Disease Resistance Gene, Xa21", Science, vol. 270, Dec. 15, 1995, pp. 1804-1806.

Staskawicz et al.: "Molecular Genetics of Plant Disease Resistance", Science, vol. 268, May 5, 1995, pp. 661-667.

Chen et al.: "Activation of protein phosphatase 5 by limited proteolysis or the binding of polyunsaturated fatty acids to the TPR domain", FEBS Letters, vol. 400, 1997, pp. 136-140.

Loh et al.: "The Pto Bacterial Resistance Gene and the Fen Insecticide Sensitivity Gene Encode Functional Protein Kinases with Serine/Threonine Specificity", Plant Physiol., vol. 108, 1995, pp. 1735-1739.

Mes et al.: "Biological and Molecular Characterization of Fusarium oxysporum f. sp. lycopersici Divides Race 1 Isolates into Separate Virulence Groups", Phytopathology, vol. 89, No. 2, 1999, pp. 156-160.

Chen et al.: "Ras-15A protein shares highly similar dominant-negative biological properties with Ras-17N and forms a stable, guanine-nucleotide resistant complex with CDC25 exchange factor", Oncogene, vol. 9, 1994, pp. 2691-2698.

Keen: "Gene-For-Gene Complementary in Plant-Pathogen Interactions", Annu. Rev. Genet., vol. 24, 1990, pp. 447-463.

Flor: "Current Status of the Gene-For-Gene Concept", Annu. Rev. Phytopathol., vol. 9, 1971, pp. 275-296.

Memelink: "Two-yeast/*Escherichia coli*/plasmid vectors designed for yeast one and two-hybrid screens that allow directional cDNA cloning", Elsevier Trends Journals Technical Tips Online, Apr. 2000.

\* cited by examiner

Interactor K-10 (diaphanous homolog)>> I-2 construct A

```
    TAT CTA TTC GAT GAT GAA GAT ACC CCA AAC CCA AAA AAA GAG ATC TCT ATG GCT TAC CCA TAC GAT GTT      75
  1 Y   L   F   D   D   E   D   T   P   N   P   K   K   E   I   S   M   A   Y   P   Y   D   V       25

76 CCA GAT TAC GCT AGC TTG GGT CAT ATG GCC ATG GAG GCC CCG GGG ATC CGA ATT CGG CAC GAG GCA GCA CGT 150
 26 P   D   Y   A   S   L   G   H   M   A   M   E   A   P   G   I   R   I   R   H   E   A   A   R   50

151 AAA TTA AGA GAG AAC CAA AGC ACT ACC AGT GTA CAG GAA GAT CTT GTA GAA GAT CCT GCT CAG GAG TCG GCA 225
 51 K   L   R   E   N   Q   S   T   T   S   V   Q   E   D   L   V   E   D   P   A   Q   E   S   A   75

226 GAT TAT CAT CGT AAC CTT GGT CAA AGC ACT CGT ATG AAG CTT GTA GAA GAT CCT GCT CAG GAG TCG GCA      
    GAT TAT CAT CGT AAC CTT GGT CAA ATG GTT TCT GGT TTA AGC AAC GAG CTT GAG AAT GTA AGA AAA GCT TCA 300
 76 D   Y   H   R   N   L   G   Q   M   V   S   G   L   S   N   E   L   E   N   V   R   K   A   S   100

301 CTT ATT GAC GGC GAG AAC TTA AGT GCA GCT GTC ATG AAG CTT AAT CAC TCA CTC ATG AAA ACT AAA GAG TTT CTG 375
101 L   I   D   G   E   N   L   S   A   A   V   M   K   L   N   H   S   L   M   K   T   K   E   F   L  125

376 GAC ACT GAT ATG AGA AGT TTG GAG GAT GAA AGT AAG TTC CGT GAT ACA CTC ACA AAT TTT ATC CAA CAT GCG GAA 450
126 D   T   D   M   R   S   L   E   D   E   S   K   F   R   D   T   L   T   N   F   I   Q   H   A   E  150

451 CAG GAC ATT ACT TGC ATA CTA GAA GAG AAA AAG ATA ATG TCT TTG GTT AAG AGC ACA GAT TAC TTC CAT      525
151 Q   D   I   T   C   I   L   E   E   K   K   I   M   S   L   V   K   S   T   G   D   Y   F   H   175

526 GGA AAT TCA GGG AAG GAT GAA GGC TTG CGT CTC TTT TCA GTC GTT AGT GAT TTC TTG ATT ATG TTG GAC AAG GCA 600
176 G   N   S   G   K   D   E   G   L   R   L   F   S   V   V   S   D   F   L   I   M   L   D   K   A  200

601 TGT ACA GTG GTG AGA AAC TCA ACG AAG TTA CCA GTT AAG ATT CCT AAA AAA GGG ACA TTA ACA TCT CCT TCC CAA 675
201 C   T   V   V   R   N   S   T   K   L   P   V   K   I   P   K   K   G   T   L   T   S   P   S   Q  225
```

FIGURE 1A

```
676 GAA TCC TGT CCT GAG TCT TTG CAA GAC ATA CGT AAA CAA CTA TTT CCT GCA ATC CAG GAG CGA CAG ATG CAC TAT 750
226 E   S   C   P   E   S   L   Q   D   I   R   K   Q   L   F   P   A   I   Q   E   R   Q   M   H   Y   250

751 TCT AGT TCA GAC GAC GAG AGC TCA AGC CCG TAG ctgtctattagttggtcagagtacttggagctaatatggcttgatatagtcca 839
251 S   S   S   D   D   E   S   S   S   P   *                                                        261

840  cagaagtatgtatttaacgactatatgaggcctaagtgtgctcctacaccagttagcaaacacatgtctacagagatagagtgaatagacattttgc 939
940  ttcaatgatctcttgagtcctagcactagcggtaggaagaatgcatagtagtattgcatgtcttactacaagatccacaga 1039
1040 gttaaaccacagcgctctcactgtctgagtcacctttatctatataacaatccaaatatcgagatggtaatgtactgaatctcctaaatatttgttaaat 1139
1140 tatatttagtatgtattggaagttagaccagattcgtagtagtttcagctctcttttctcgtcaaaaaaaaaaaaaactgagagatctatgaatc 1239
1240 gtagatactgaaaaacccc 1258
```

FIGURE 1B

Interactor K-23 (TPR-kinesin) >> I-2 construct A

```
    CTT GCC GCC ACT TAT GAT GCT ATA GGA AGA GTG GAT GAT ATT GAG GCT ATT CTG GAG TAC GTT CTT AAA CTG    75
  1 L   A   A   T   Y   D   A   I   G   R   V   D   D   I   E   A   I   L   E   Y   V   L   K   L     25

76 AGA GAA GAA AAA CTC GGA ACT GCA AAT CCT GAT TTC AAC GAT GAG AAA AAG AGG CTG GCT GAA TTA TTG AAA GAA  150
 26 R   E   E   K   L   G   T   A   N   P   D   F   N   D   E   K   K   R   L   A   E   L   L   K   E  50

151 GCA GGT AGA TCT CGG AAC AAA AAC CCG AAT TCC TTA GAA AAT CTT ATT GAT CCA AAC TCT AAA AGG ACG AAG  225
 51 A   G   R   S   R   N   K   N   P   N   S   L   E   N   L   I   D   P   N   S   K   R   T   K     75

226 AAA GAG ACT TCA TCA AAG AAG TGG TCT GCA TTT GGC TTC AGA AGT TGA ttctttctagcaagaagttttctataacattgtaa  309
 76 K   E   T   S   S   K   K   W   S   A   F   G   F   R   S   *                                       91

310 aggcacgaatgtgtgttatgtttatgtcactataaactggtgaagctattggttgtgtcctttgaattcatgtcattatctcttttttcattcat      409

410 tgcttgattgttatcagtttgaatttgatgatgtttcaacaaaccatcaatgtttatggaagtaaaaaaaaaaaaaaaaaaaa                  505
```

FIGURE 2

Interactor K-6 (Translin) >> I-2 construct A

```
     ATT CGG CAC GAG GCG GAC TTG ACA GGA GAA TTA ATG AGG TTA GCA ATC GGT CGA ATT TCA GAA GGG GAA CTT    75
     I   R   H   E   A   D   L   T   G   E   L   M   R   L   A   I   G   R   I   S   E   G   E   L     25

76  GAT TTT GCA GAG AAG ATC TGC AGT TTT GCG GAA ATT TAC AGG AAC CTT ACT CTT ATT GCC CCA GAG ATG GAT   150
 26  D   F   A   E   K   I   C   S   F   A   E   I   Y   R   N   L   T   L   I   A   P   E   M   D     50

151  GAT AGT TCA GAC ATG AAA CAG AGT GTG ATG AAG ATA GAA AAT GCT TGT TTT AGT                           225
 51  D   S   S   D   M   K   Q   S   V   M   K   I   E   N   A   C   F   S                              75

226  GTT CAT GTA AGA GGA TCG GAG TAT ATT CCC CTT CTT GGA CCT GCT GAT ACC AGT TAT CCA CTG TTG GGC ATG CCA 300
 76  V   H   V   R   G   S   E   Y   I   P   L   L   G   F   A   D   T   S   Y   P   L   L   G   M   P   100

301  GAC ATT GAA TGA agaagcacgaaagataagttcctgttgtttgctgttgaagtgttgatgcagctctccagcctgcatatacacggggcagagc 396
101  D   I   E   *                                                                                      104

397  gtctttgtgggctgcacttccgcatgtgctttggtgcaagtactttgcatcttcgtatttgaaattgacacatttgtaattactcc              496

497  agtccacctagtgaactttatgcgactttgtagcggagattgtataggcttacaagtactctatctcctactgacctacaagatgatacctttt      596

597  tgcgaaatgttgcagagtttgttttctgagatgattttagactagtacacactctttattaccagaaggtattctgaatcaatgttctttttgttg    696

697  ttattattgtatttcatagctttgaaacttaaaaaaaaaaaaaaaaaa                                                    747
```

FIGURE 3

Interactor J-49 (Hsp17) ) >> I-2 construct B

```
  1 cgaattcgcacgagaaaaacgtagaaattctcaaaagttcactgaaa ATG TCT CTG ATC CCA AGA ATT TTC GGC GAT CGA CGA    87
                                                    M   S   L   I   P   R   I   F   G   D   R   R     12

88 AGC AGC AGC ATG TTC GAT CCA TTT TCA ATT GAC GTA TTT GAT CCA TTC AGG GAA TTA GGC TTC CCA AGT ACC AAT   162
 13  S   S   S   M   F   D   P   F   S   I   D   V   F   D   P   F   R   E   L   G   F   P   S   T   N    37

163 TCA GGG GAG AGC TCT GCA TTT GCC ACC ACA ATA GAC TGG AAG GAA ACT CCA GAA GCT CAT GTG TTC AAG GTT   237
 38  S   G   E   S   S   A   F   A   T   T   I   D   W   K   E   T   P   E   A   H   V   F   K   V    62

238 GAT CTT CCA GGG CTT AAG AAG GAG GTC AAA GTG GAA GTC GAG GAG GAA ATA GGG GT                        296
 63  D   L   P   G   L   K   K   E   V   K   V   E   V   E   E   E   I   G                             81
```

FIGURE 4

Interactor S-25 (PP5, TPR-Phosphatase) >> I-2 construct B

```
  1 tgaattcggcacgagagcgaacatctactcagccagctcagtgcat:gt ATG CCT GGT ATG GAA GCT GAG AAC TCA AGC GCC    87
                                                      M   P   G   M   E   A   E   N   S   H   A      11

88 TCC CGA GCT GAA GAA CTC AAG CAA CTC GCA AAT GAA GCA TTC AAA GGG CCT AAG TAT TCG CAA GCT ATT GAT CTG    162
 12  S   R   A   E   E   L   K   Q   L   A   N   E   A   F   K   G   H   K   Y   S   Q   A   I   D   L     36

163 TAC ACA CAA GCG ATT GAG TTG AAC GGT GAG AAT GCG GTG TAC TAT GCT AAC CGT GCG TTT GCT CAC ACC AAA TTG    237
 37  Y   T   Q   A   I   E   L   N   G   E   N   A   V   Y   Y   A   N   R   A   F   A   H   T   K   L     61

238 GAG GAA TAT GCT AGC GCA ATA CAG GAT GGA ACT AGA TAT GCT ATT GAA ATT GAC CCT AGA TAT TCA AAG GGT TAT TAT    312
 62  E   E   Y   A   S   A   I   Q   D   G   T   R   Y   A   I   E   I   D   P   R   Y   S   K   G   Y   Y     86

313 ACG AGA GGA GCT GCA TAT TTG GCA ATG GGG AAG TTC AAA GAT GCA CTC AAG GAT TTT CAA CAG GTC AAA AAA TTA    387
 87  R   R   G   A   A   Y   L   A   M   G   K   F   K   D   A   L   K   D   F   Q   Q   V   K   K   L    111

388 TGT CCA AAC GAC CCA GAT GCT ACC AAA AAA TTG AAG GAA TGT GAG AAA GCT GTC ATG AAG CTA AAA TTT GAA GAA    462
112  C   P   N   D   P   D   A   T   K   K   L   K   E   C   E   K   A   V   M   K   L   K   F   E   E    136

463 GCT ATT TCT GTC CCA GAA TCT CAG CGT CGA TCA GTA GCT GAT TCT ATT GAT TAT CGT TCT GTA GAG GTG GAG CCT    537
137  A   I   S   V   P   E   S   Q   R   R   S   V   A   D   S   I   D   Y   R   S   V   E   V   E   P    161

538 CAA TAT GCT GGT GCA AGA ATA GAG GGA GAT GTT GTA ACA TTA GAT GTT CTG CAA ATA GTA TAT CAG ATT GTG CTG    612
162  Q   Y   A   G   A   R   I   E   G   D   V   V   T   L   D   V   L   Q   I   V   L   Q   T   R   E    186

613 AAC CAG AAG AAC TTG CAT AAG AGG TAT GCC TAC AAG ATG CTA GAT GAT TTC GTT AAG AGA ACA AGA GAA ATG TTG CGA GCA CTG CCC    687
187  N   Q   K   N   L   H   K   R   Y   A   Y   K   M   L   D   D   F   V   K   R   T   R   E   M   L   R   A   L   P    211

688 TCC CTT GTT GAC ATT GTT CCC GAA GGG AAG CAC TTC ACT GTA TGT GGT GAT GTA CAT GGT CAG TTT TAT GAC    762
212  S   L   V   D   I   V   P   E   G   K   H   F   T   V   C   G   D   V   H   G   Q   F   Y   D    236
```

FIGURE 5A

```
 763 CTC CTA AAT ATT TTC GAG CTC CTC AAT GGG CTT CCA TCA GAA GAC AAT CCG TAT CTG TTC AAT GGT GAT TTT GTT GAT  837
 237  L   L   N   I   F   E   L   L   N   G   L   P   S   E   D   N   P   Y   L   F   N   G   D   F   V   D   261

838 AGA GGG TCT TTC TCT CTA GAG GTC ATA TTG ACA TTA TTT GCC TTC AAG TGC ATG TGT CCA TCA GCT ATA CAC CTG       912
 262  R   G   S   F   S   L   E   V   I   L   T   L   F   A   F   K   C   M   C   P   S   A   I   H   L      286

913 GCG AGA GGA AAT CAC GAA AGC AAG ATG AAC AAA ATA TAT GGG TTT GAG GGC GAG GTC AGA TCC AAG TTA AGT          987
 287  A   R   G   N   H   E   S   K   M   N   K   I   Y   G   F   E   G   E   V   R   S   K   L   S          311

988 GAA ATA TTT GTG GAA CTC TTT GCA GAA GTG TTC TGC TTA CCT TTG GCC CAT GTC ATA AAT GAG AAA GTC TTT         1062
 312  E   I   F   V   E   L   F   A   E   V   F   C   C   L   P   L   A   H   V   I   N   E   K   V   F     336

1063 GTA GTA CAT AGA GGT CTT TTT AGT GTT GAT GGC AAG CTC TCT GAT ATT AGA GCA ATT GAT CGG TTT TGT GAG         1137
 337  V   V   H   R   G   L   F   S   V   D   G   K   L   S   D   I   R   A   I   D   R   F   C   E        361

1138 CCC CCA GAA GAG GGG CTT ATG TGT GAA TTG TTG TGG AGT GAT CCA CAA CCT CAG CCT GGT AGA GGA CCT AGT AAA    1212
 362  P   P   E   E   G   L   M   C   E   L   L   W   S   D   P   Q   P   Q   P   G   R   G   P   S   K    386

1213 CGA GGT GTT GGT CTT TCT TTC GGG GGA GAC GTA ACT AAA AGA TTC TTG CAG GAA AAT CTA GAT CTA GTG GTG         1287
 387  R   G   V   G   L   S   F   G   G   D   V   T   K   R   F   L   Q   E   N   N   L   D   L   V   V     411

1288 CGA TCT CAT GAA GTG AAG GAT GAA GGT TAT GAG ATT GAG CAT GAC GGC AAA CTC ATA ACG GTG TTT TGC GCT CCC    1362
 412  R   S   H   E   V   K   D   E   G   Y   E   I   E   H   D   D   G   K   L   I   T   V   F   C   A   P  436

1363 AAT TAT TGT GAC CAG ATG GGT AAC AAG GGT GCT TTT ATA CGA TTT GAG GCT CCC GAT ATG AAG CCA AAT ATT GTG    1437
 437  N   Y   C   D   Q   M   G   N   K   G   A   F   I   R   F   E   A   P   D   M   K   P   N   I   V    461

1438 ACA TTT TCA GCA GTG CCA CAT CCT GAT GTC AAA CCA ATG GCA TAT GCC AAC TTC CTT CGC ATG TTT TCT TAA        1512
 462  T   F   S   A   V   P   H   P   D   V   K   P   M   A   Y   A   N   F   L   R   M   F   S   *        486

1513 aaactctggaacctaacgttcagtattacaatgatgactgactcaggagcatacacatcaggaggcaaaagagctagtacttacag                  1612
1613 ccaattagctgcagtgcattattcgcccagcagtgaggatcctcacctcctttgtttgattaaggcgtaaacacttttc                         1712
1713 tctacgataacatgtcgtgtvgattgtcctcctgtattattcctttgtaagattgttacacttccattccttcttttagaatgttcaaatt             1812
1813 gggaaagctttgataagtcgaatttgtttttctaaaaaaaaaaaaaaaaaa                                                     1885
```

| | | | |
|---|---|---|---|
| K10 | 104 | CHAEQDCHLREADFKWLKRVQAQETLAMSLVKEITEYFHG | 133 |
| A. th. k10 | 615 | ERADFKWLKRVQAQETLAMSLVKEITEYFHG | 644 |
| A. th formin 1 | 932 | KRAEEEIRVQAQETLAMSLVKEITEYFHG | 961 |
| N. tab. formin | 730 | KVAEEDIARLQQSEENRAFSLVRETFHG | 759 |
| P. mar. formin | 13 | QEAAEELKKEREEGSTLFAVKKITEYFHV | 42 |
| A. th formin 2 | 775 | ETAAEELKKEREEGSTLFAVKKITEYFHV | 804 |
| | | | |
| K10 | 134 | NSGDEG··LRLFSVVSDFEIMLDKACTVV | 161 |
| A. th. k10 | 645 | KSAKNEG··LRLFATVRDFLIMLEKVCREV | 672 |
| A. th formin 1 | 962 | NSAKEEAHPFFLFMVRDFLGVVDRVCKEV | 991 |
| N. tab. formin | 760 | DSAREEAHPFFEMVKDFEMVDCVRCKEV | 789 |
| P. mar. formin | 43 | DAKEEGRPFFYVKRFLGMLDQVCRETT | 72 |
| A. th formin 2 | 805 | DPAKEEAQLEKVTVRDFHKLEGVCKKM | 834 |
| | | | |
| K10 | 162 | RNSTKLPVKDPKGTLTSRSQESCPESLQD | 191 |
| A. th formin 1 | 673 | KETIKTTNHSGVKESEMTTSDS·NQPSPD | 700 |
| A. th formin 1 | 992 | G·····MINERTMVSSAHKF·PVPIVNP | 1012 |
| N. tab. formin | 790 | G·····TINERTIVSSAQKF·PVPIVNP | 810 |
| P. mar. formin | 73 | G·····KTRTRMAQSSRPP·QVMAHA | 93 |
| A. th formin 2 | 835 | E·····VTSSLA··········· | 841 |
| | | | |
| K10 | 192 | LRKQLFPAQERQMHYSSDDESSP | 217 |
| A. th formin 1 | 701 | FRQRLFRAAERRMD·SSDDSEEDSSP | 729 |
| A. th formin 1 | 1013 | MMPQPLRGLVGRRQS·SSSSSDSTSSDE | 1041 |
| N. tab. formin | 811 | NLQPMISGFRAKRLH·SSSDDESSP··· | 835 |
| P. mar. formin | 94 | SMPILFRKALQRRPD·SSDDESSSP··· | 117 |
| A. th formin 2 | 0 | ············ | 841 |

```
K6              1   - - - - - - - - - - - - - - - - - - - - - - - - - - - - - -    0
A. th. translin 1   - - - - - - - - - - - - - - - - - - - - - - - M L S C S S S    7
O. sat. translin 1  M L P L R G C H R R L L S L R G V T A P S L L P P I T T T P   30

K6              1   - - - - - - - - - - - - - - - - - - - - - - - - - - - - - -    0
A. th. translin 8   A F Q R V A F M L M A P K L K P Q R L H Q M L I S N D G F G   37
O. sat. translin 31 T T S M A A P Q S H S H P A K T L R A S P P P P S T A G S A   60

K6              1   - - - - - - - - - - - - - - - - - - - - - - - - - - - - - -    0
A. th. translin 38  V C V V A E S G V E H L V K K A R T M S T E S S M K D A F S   67
O. sat. translin 61 P K R S R T M A T D A A A T A H S A S A G C S A M K A E F A   90

K6              1   - - - - - - - - - - - - - - - - - - - - - - - - - - - - - -    0
A. th. translin 68  T Y A D Y L N N F N E K R E R V K V S R D I T M N S K K V   97
O. sat. translin 91 K H A E Y L N T L N D K R E R L V K A S R D L T M N S K K A  120

K6              1   - - - - - - - - - - - - - - - - - - - - - - - - - - - - - -    0
A. th. translin 98  I F Q V H R L S K D N K E E V L E K A G K D L E A V R D Q H  127
O. sat. translin 121 L F Q V H R I S K N N K E E V L S K A E N D L T V V N Q Y   150

K6              1   - - - - - - - - - - - - - - - - - - - - - - - - - - - - - -    0
A. th. translin 128 F A R L M K E L Q G T D F W K L R R A Y S P G V Q E Y V E A  157
O. sat. translin 151 I G K L V K E L Q G T D F W K L R R A Y T F G V Q E Y V E A  180

K6              1   - - - - - - - - - - - - - - - - - - - - - - - - - - - - - -    0
A. th. translin 158 A T F Y K F C L S G T L C T L D E I N T T L V P L S D P S L  187
O. sat. translin 181 A T F C R F C K T G T L L S L A E I N D S L L E L G D K S V  210
```

|  |  | | |
|---|---|---|---|
| K6 | 1 | ----------EPLQINILDY-LGLADIIGEMRLAIGRMS | 16 |
| A. th. translin | 188 | EPLQINVLDYVLGVADLTGELMRMAIGRIS | 217 |
| O. sat. translin | 211 | EPLQINVLDYVLGVADLSGELMRLAIGRIS | 240 |
| K6 | 17 | EGELDRAEKICSFAREFYRNLTLIAPEMDD | 46 |
| A. th. translin | 218 | DGEIEFAQRIQQFVRQTHRELMLVPKMDD | 247 |
| O. sat. translin | 241 | DGEVEYAKNLQAFVRDIYRELLVPLMDD | 270 |
| K6 | 47 | SSDMKQKMETMLGSVMKIENACFSVHVRGS | 76 |
| A. th. translin | 248 | SYDMKISKMETMLQSVKIENACFSVHVRGL | 277 |
| O. sat. translin | 271 | NSEMKKKMETMLQSVKIENACFSVHVRGS | 300 |
| K6 | 77 | EYIPILG-PADTSYPLLGMPDIE- | 98 |
| A. th. translin | 278 | EYIPELG-PADTSYPLLGMPDIE- | 299 |
| O. sat. translin | 300 | -DNAPTSYLEGAADVE- | 300 |

FIGURE 8B

```
k23         1  - - - - - - - - - - - - - - - - - - - - - - - - - - - - -                                                0
A. th. KLC1 362  T G K L R E S K S Y C E N A L R I Y N K P V P G T T V E E I                                          391
A. th. KLC2 471  T G K V R E A K S Y C E N A L R I Y E S H N L E I S P E E I                                          500 k23         1  - - - - - - - - - - - - - - - - - - - - - - - - - - - - -                                                0
A. th. KLC1 392  A G G L T E I S A I Y E S V D E P E E A L K L L Q K S M K L                                          421
A. th. KLC2 501  A S G L T D I S V I C E S M N E V E Q A I T L L Q K A L K I                                          530 k23         1  - - - - - - - - - - - - - - - - - - - - - - - - - - - - -                                                0
A. th. KLC1 422  L E D K P G Q Q S A I A G L E A R M G V M Y Y T V G R Y E D                                          451
A. th. KLC2 531  Y A D S P G Q K I M I A G I E A Q M G V L Y Y M M G K Y M E                                          560 k23         1  - - - - - - - - - - - - - - - - - - - - - - - - - - - - -                                                0
A. th. KLC1 452  A R N A F E S A V T K L R A A G E K - S A F F G V V L N Q M                                          480
A. th. KLC2 561  S Y N T F K S A I S K L R A T G K K Q S T F F G I A L N Q M                                          590 k23         1  - - - - - - - - - - - - - - - - - - - - - - - - - - - - -                                                0
A. th. KLC1 481  G L A C V Q L F K I D E A G E L F E E A R G I L E Q E R G P                                          510
A. th. KLC2 591  G L A C I Q L D A I E E A V E L F E E A K C I L E Q E C G P                                          620 k23         1  - - - - - - R H E L A A T Y D A L G R V D D A I E L L E                                               23
A. th. KLC1 511  C D Q D T L G V Y S N L A A T Y D A M G R I E D A I E L L E                                          540
A. th. KLC2 621  Y H P E T L G L Y S N L A G A Y D A L G R L D D A L K L L G                                          650 k23         24  Y V L K L R E E K L G T A N P D F N D E K K R L A E L L K E                                           53
A. th. KLC1 541  Q V L K L R E E K L G T A N P D F E D E K K R L A E L L K E                                          570
A. th. KLC2 651  H V M G V R E E K L G T A N R V T E D E K R R L A Q L K K E                                          680 k23         54  A G R S R N K N P N S I E N L D P N S K R T T K K E T S S                                             83
A. th. KLC1 571  A G R S R N Y K A K S E Q N L I D P N - A R P P K K E S S A                                          599
A. th. KLC2 681  A G N V T G R K A K                                                                                 690 k23         84  K K W S A F Q F R S                                                                                   93
A. th. KLC1 600  K K W P S L G E K F                                                                                 609
```

FIGURE 9

| | | | |
|---|---|---|---|
| S25 | 1 | - - M E A E N S N A S R A E L K Q L A N E R A E L K G H K Y S | 28 |
| A.th PP5 | 1 | M E T K N E N S D V B R A E F K S Q A N E A F K G H K Y S | 30 |
| S25 | 29 | Q A I D L Y T Q A I E Y N G E N A V Y Y A N R A F A H T K L | 58 |
| A.th PP5 | 31 | S A I D L Y T K A I E L N S N N A V Y W A N R A F A H T K L | 60 |
| S25 | 59 | E E Y G S A I Q D G T R A E I D P R Y S K G Y M R R G A A | 88 |
| A.th PP5 | 61 | E E Y G S A I Q D A S I K A I E V D S R Y S K G Y Y R R G A A | 90 |
| S25 | 89 | Y L A M G K F K D A L K D F Q Q V K L C P N D P D A T K K | 118 |
| A.th PP5 | 91 | M E A M G K F K D A L K D F Q Q V K R L S P N D P D A T R K | 120 |
| S25 | 119 | L K E C E K A V M K L K E E A I S V P E S Q R R S V A D S | 148 |
| A.th PP5 | 121 | L K E C E K A V M K L K E E A I S V P V S E R R S V A E S | 150 |
| S25 | 149 | I D Y R - - - - - - - - - - - - - - - - - - - - - - - | 152 |
| A.th PP5 | 151 | D F H T I G N K P R S S S M P T K T A L A A V V A A V M V | 180 |
| S25 | 153 | - - - - - - - - - - - - - - - - - - - - - S V E V E R Q | 159 |
| A.th PP5 | 181 | V A V R G F A T T E I L M V L V S V V L G T F W W E V E R Q | 210 |
| S25 | 160 | Y A G A R I E G D V V T L D F Y K K M L D D F K N Q K N L H | 189 |
| A.th PP5 | 211 | S G A R I E G E E V T L D F V K T M M E D F K N Q K T L H | 240 |
| S25 | 190 | K R Y A Y Q I V L E Q T R E M R A L P S G V D V P E G K | 219 |
| A.th PP5 | 241 | K R Y A Y Q I V L E Q T R Q I L A L P S L V D I S V P H G K | 270 |
| S25 | 220 | H F T V C G D V H G Q F Y D L N I E L N G L P S E D N P | 249 |
| A.th PP5 | 271 | H I T V C G D V H G Q F Y D L N I F E L N G L P S E E N P | 300 |
| S25 | 250 | Y L F N G D F W D R G S H E V L T I F A F K C M C P S | 279 |
| A.th PP5 | 301 | Y L F N G D F V D R G S H S V E T I L L L A F K C M C P S | 330 |

FIGURE 10A

| | | | |
|---|---|---|---|
| S25 | 280 | ATHLARGNHESKSMNKLGFEGEVRSKLSE | 309 |
| A.th PP5 | 331 | SIYLARGNHESKSMNKIGFEGEVRSKLSE | 360 |
| S25 | 310 | IFVELFAEVFCCLPLAHVINEKVFVHRGL | 339 |
| A.th PP5 | 361 | KFVDLFAEVFGYLPLAHVINGKVFVHGGL | 390 |
| S25 | 340 | FSVDGVKLSDIRAIDRFQEPPEEGLMCELL | 369 |
| A.th PP5 | 391 | FSVDGVKLSDIRAIDRFQERPEEGLMQELL | 420 |
| S25 | 370 | WSDPQPQPGRGPSKRGVGLSFGGDVIKRFL | 399 |
| A.th PP5 | 421 | WSDPQPLPGRGPSKRGVGLSFGGDVTKRFL | 450 |
| S25 | 400 | QENLEDLIVRSHEVKDEGYEIEHDGKLITV | 429 |
| A.th PP5 | 451 | QDNNLEDLIVRSHEVKDEGYEVEHDGKLITV | 480 |
| S25 | 430 | FSAPNYCDQMGNKGAFIRFEAPDMKPNIVT | 459 |
| A.th PP5 | 481 | FSAPNYCDQMGNKGAFIRFEAPDMKPNIVT | 510 |
| S25 | 460 | FSAVPHPDVKPMAYANNFLRMFS | 482 |
| A.th PP5 | 511 | FSAVPHPDVKPMAYANNFLRMFN | 533 |

FIGURE 10B

SEQUENCE LISTING

```
<160> NUMBER OF SEQ ID NOS: 28

<210> SEQ ID NO 1
<211> LENGTH: 1255
<212> TYPE: DNA
<213> ORGANISM: Lycopersicon esculentum
<220> FEATURE:
<221> NAME/KEY: CDS
<222> LOCATION: (1)..(777)
<220> FEATURE:
<221> NAME/KEY: misc_feature
<222> LOCATION: Complement((1)..(1255))
<223> OTHER INFORMATION: Interactor K-10

<400> SEQUENCE: 1 tat cta ttc gat gat gaa gat acc cca cca aac cca aaa aaa gag atc      48
Tyr Leu Phe Asp Asp Glu Asp Thr Pro Pro Asn Pro Lys Lys Glu Ile
  1               5                  10                  15 tct atg gct tac cca tac gat gtt cca gat tac gct agc ttg ggt ggt      96
Ser Met Ala Tyr Pro Tyr Asp Val Pro Asp Tyr Ala Ser Leu Gly Gly
             20                  25                  30 cat atg gcc atg gag gcc ccg ggg atc cga att cgg cac gag gca gca     144
His Met Ala Met Glu Ala Pro Gly Ile Arg Ile Arg His Glu Ala Ala
         35                  40                  45 cgt aaa tta aga gag aac caa agc act acc agt gta cag aca gaa gat     192
Arg Lys Leu Arg Glu Asn Gln Ser Thr Thr Ser Val Gln Thr Glu Asp
 50                  55                  60 ctt gta gaa gat cct gct cag gag tcg gca gat tat cat cgt aac ctt     240
Leu Val Glu Asp Pro Ala Gln Glu Ser Ala Asp Tyr His Arg Asn Leu
 65                  70                  75                  80 ggt ctt cag atg gtt tct ggt tta agc aac gag ctt gag aat gta aga     288
Gly Leu Gln Met Val Ser Gly Leu Ser Asn Glu Leu Glu Asn Val Arg
                 85                  90                  95 aaa gct tca ctt att gac ggc gag aac tta agt gca gct gtc atg aag     336
Lys Ala Ser Leu Ile Asp Gly Glu Asn Leu Ser Ala Ala Val Met Lys
            100                 105                 110 ctt aat cac tca ctc atg aaa act aaa gag ttt ctg gac act gat atg     384
Leu Asn His Ser Leu Met Lys Thr Lys Glu Phe Leu Asp Thr Asp Met
        115                 120                 125 aga agt ttg gag gat gaa agt aag ttc cgt gat aca ctc aca aat ttt     432
Arg Ser Leu Glu Asp Glu Ser Lys Phe Arg Asp Thr Leu Thr Asn Phe
    130                 135                 140
```

-continued

| | | |
|---|---|---|
| atc caa cat gcg gaa cag gac att act tgc ata cta gaa gaa gag aaa<br>Ile Gln His Ala Glu Gln Asp Ile Thr Cys Ile Leu Glu Glu Glu Lys<br>145                     150                     155                     160 | | 480 |
| aag ata atg tct ttg gtt aag agc aca gga gat tac ttc cat gga aat<br>Lys Ile Met Ser Leu Val Lys Ser Thr Gly Asp Tyr Phe His Gly Asn<br>                   165                     170                     175 | | 528 |
| tca ggg aag gat gaa ggc ttg cgt ctc ttt tca gtc gtt agt gat ttc<br>Ser Gly Lys Asp Glu Gly Leu Arg Leu Phe Ser Val Val Ser Asp Phe<br>         180                     185                     190 | | 576 |
| ttg att atg ttg gac aag gca tgt aca gtg gtg aga aac tca acg aag<br>Leu Ile Met Leu Asp Lys Ala Cys Thr Val Val Arg Asn Ser Thr Lys<br>               195                     200                     205 | | 624 |
| tta cca gtt aag att cct aaa aaa ggg aca tta aca tct cct tcc caa<br>Leu Pro Val Lys Ile Pro Lys Lys Gly Thr Leu Thr Ser Pro Ser Gln<br>210                     215                     220 | | 672 |
| gaa tcc tgt cct gag tct ttg caa gac ata cgt aaa caa cta ttt cct<br>Glu Ser Cys Pro Glu Ser Leu Gln Asp Ile Arg Lys Gln Leu Phe Pro<br>225                     230                     235                     240 | | 720 |
| gca atc cag gag cga cag atg cac tat tct agt tca gac gac gag agc<br>Ala Ile Gln Glu Arg Gln Met His Tyr Ser Ser Ser Asp Asp Glu Ser<br>                     245                     250                     255 | | 768 |
| tca agc ccg tagctgtcta tttaggtgtc agagtacttt ggagctaata<br>Ser Ser Pro | | 817 |
| tggcttggat aatagtccac agaagtatgt atttaacgac tatatgaggc ctaaggtgtg | | 877 |
| cctcctacac ccagttagca aacacatgct ctacgagata gagtgaatag acattttgct | | 937 |
| tcaatgatct cttcgagtcc tagcactagc ggtaggaaga atggctatag tatagatgcc | | 997 |
| atagtagtta ttgcatggtc tactacaacg atccacagag ttaaaccaca gcctctcact | | 1057 |
| gtctgtagtc acctttatct ataacaatcc aaatatcgag atggtaatgg tactgaaatc | | 1117 |
| tcctaaatat ttgttaaatt atatttagta tgtattggaa gttagaccag attcgtatag | | 1177 |
| tttcagcttc tttttctcgt caaaaaaaaa aaaaaaaaa ctcgagagat ctatgaatcg | | 1237 |
| tagatactga aaacccc | | 1255 |

<210> SEQ ID NO 2
<211> LENGTH: 259
<212> TYPE: PRT
<213> ORGANISM: Lycopersicon esculentum

<400> SEQUENCE: 2

Tyr Leu Phe Asp Asp Glu Asp Thr Pro Pro Asn Pro Lys Lys Glu Ile
1                   5                   10                  15

Ser Met Ala Tyr Pro Tyr Asp Val Pro Asp Tyr Ala Ser Leu Gly Gly
               20                   25                   30

His Met Ala Met Glu Ala Pro Gly Ile Arg Ile Arg His Glu Ala Ala
            35                   40                   45

Arg Lys Leu Arg Glu Asn Gln Ser Thr Thr Ser Val Gln Thr Glu Asp
    50                   55                   60

Leu Val Glu Asp Pro Ala Gln Glu Ser Ala Asp Tyr His Arg Asn Leu
65                   70                   75                   80

Gly Leu Gln Met Val Ser Gly Leu Ser Asn Glu Leu Glu Asn Val Arg
               85                   90                   95

Lys Ala Ser Leu Ile Asp Gly Glu Asn Leu Ser Ala Ala Val Met Lys
            100                 105                110

Leu Asn His Ser Leu Met Lys Thr Lys Glu Phe Leu Asp Thr Asp Met
        115                   120                125

```
Arg Ser Leu Glu Asp Glu Ser Lys Phe Arg Asp Thr Leu Thr Asn Phe
    130                 135                 140

Ile Gln His Ala Glu Gln Asp Ile Thr Cys Ile Leu Glu Glu Glu Lys
145                 150                 155                 160

Lys Ile Met Ser Leu Val Lys Ser Thr Gly Asp Tyr Phe His Gly Asn
                165                 170                 175

Ser Gly Lys Asp Glu Gly Leu Arg Leu Phe Ser Val Val Ser Asp Phe
            180                 185                 190

Leu Ile Met Leu Asp Lys Ala Cys Thr Val Val Arg Asn Ser Thr Lys
                195                 200                 205

Leu Pro Val Lys Ile Pro Lys Lys Gly Thr Leu Thr Ser Pro Ser Gln
    210                 215                 220

Glu Ser Cys Pro Glu Ser Leu Gln Asp Ile Arg Lys Gln Leu Phe Pro
225                 230                 235                 240

Ala Ile Gln Glu Arg Gln Met His Tyr Ser Ser Ser Asp Asp Glu Ser
                245                 250                 255

Ser Ser Pro

<210> SEQ ID NO 3
<211> LENGTH: 502
<212> TYPE: DNA
<213> ORGANISM: Lycopersicon esculentum
<220> FEATURE:
<221> NAME/KEY: CDS
<222> LOCATION: (1)..(267)
<220> FEATURE:
<221> NAME/KEY: misc_feature
<222> LOCATION: Complement((1)..(502))
<223> OTHER INFORMATION: Interactor K-23 (TPR-kinesin)

<400> SEQUENCE: 3 ctt gcc gcc act tat gat gct ata gga aga gtg gat gat gct att gag      48
Leu Ala Ala Thr Tyr Asp Ala Ile Gly Arg Val Asp Asp Ala Ile Glu
  1               5                  10                  15 att ctg gag tac gtt ctt aaa ctg aga gaa gaa aaa ctc gga act gca      96
Ile Leu Glu Tyr Val Leu Lys Leu Arg Glu Glu Lys Leu Gly Thr Ala
             20                  25                  30 aat cct gat ttc aac gat gag aaa aag agg ctg gct gaa tta ttg aaa     144
Asn Pro Asp Phe Asn Asp Glu Lys Lys Arg Leu Ala Glu Leu Leu Lys
         35                  40                  45 gaa gca ggt aga tct cgg aac aaa aac ccg aat tcc tta gaa aat ctt     192
Glu Ala Gly Arg Ser Arg Asn Lys Asn Pro Asn Ser Leu Glu Asn Leu
     50                  55                  60 att gat cca aac tct aaa agg acg acg aag aaa gag act tca tca aag     240
Ile Asp Pro Asn Ser Lys Arg Thr Thr Lys Lys Glu Thr Ser Ser Lys
 65                  70                  75                  80 aag tgg tct gca ttt ggc ttc aga agt tgattctttc tagcaagaag            287
Lys Trp Ser Ala Phe Gly Phe Arg Ser
                 85 tttttctata acattgtaaa ggcacgaatg tgtgttatgt tttatgtcac tataaactgg    347 tgaagcttat tggttgttgt ccttttgaat tcatgtcatt tatctttttt ttcattcatt    407 gcttgattgt ttatcagttt gtaatttgat gatgtttctg tttcaacaaa accaatcaat    467 gtttatggaa gtaaaaaaaa aaaaaaaaaa aaaaa                               502

<210> SEQ ID NO 4
<211> LENGTH: 89
<212> TYPE: PRT
<213> ORGANISM: Lycopersicon esculentum
```

<400> SEQUENCE: 4

```
Leu Ala Ala Thr Tyr Asp Ala Ile Gly Arg Val Asp Asp Ala Ile Glu
 1               5                  10                  15

Ile Leu Glu Tyr Val Leu Lys Leu Arg Glu Glu Lys Leu Gly Thr Ala
            20                  25                  30

Asn Pro Asp Phe Asn Asp Glu Lys Lys Arg Leu Ala Glu Leu Leu Lys
        35                  40                  45

Glu Ala Gly Arg Ser Arg Asn Lys Asn Pro Asn Ser Leu Glu Asn Leu
    50                  55                  60

Ile Asp Pro Asn Ser Lys Arg Thr Thr Lys Lys Glu Thr Ser Ser Lys
65                  70                  75                  80

Lys Trp Ser Ala Phe Gly Phe Arg Ser
                85
```

<210> SEQ ID NO 5
<211> LENGTH: 744
<212> TYPE: DNA
<213> ORGANISM: Lycopersicon esculentum
<220> FEATURE:
<221> NAME/KEY: CDS
<222> LOCATION: (1)..(306)
<220> FEATURE:
<221> NAME/KEY: misc_feature
<222> LOCATION: Complement((1)..(744))
<223> OTHER INFORMATION: Interactor K-6 (Translin)

<400> SEQUENCE: 5

```
att cgg cac gag gcg gac ttg aca gga gaa tta atg agg tta gca atc      48
Ile Arg His Glu Ala Asp Leu Thr Gly Glu Leu Met Arg Leu Ala Ile
 1               5                  10                  15 ggt cga att tca gaa ggg gaa ctt gat ttt gca gag aag atc tgc agt      96
Gly Arg Ile Ser Glu Gly Glu Leu Asp Phe Ala Glu Lys Ile Cys Ser
            20                  25                  30 ttt gcg cgt gaa att tac agg aac ctt act ctt att gcc cca gag atg     144
Phe Ala Arg Glu Ile Tyr Arg Asn Leu Thr Leu Ile Ala Pro Glu Met
        35                  40                  45 gat gat agt tca gac atg aaa cag aaa atg gaa aca atg ctc cag agt     192
Asp Asp Ser Ser Asp Met Lys Gln Lys Met Glu Thr Met Leu Gln Ser
    50                  55                  60 gtg atg aag ata gaa aat gct tgt ttt agt gtt cat gta aga gga tcg     240
Val Met Lys Ile Glu Asn Ala Cys Phe Ser Val His Val Arg Gly Ser
65                  70                  75                  80 gag tat att ccc ctt ctt gga cct gct gat acc agt tat cca ctg ttg     288
Glu Tyr Ile Pro Leu Leu Gly Pro Ala Asp Thr Ser Tyr Pro Leu Leu
                85                  90                  95 ggc atg cca gac att gaa tgaagaagca cgaaagataa gttccttgtt            336
Gly Met Pro Asp Ile Glu
            100 tgctgttgaa gttgttgatg cagctctccc agcctgcata tacacacggg gcagagcgtc   396 tttgttgggc tgcacttccg catgtgcttt tgcaaggtac tttggtgcaa cgatttgcat   456 cttcgtattt gaaattgaca cattttgtaa ttactccagt ccacctagtg aactttatgc   516 gactttgtag cggagattgt ataggcttac aagtactcta tttccctcct actgacctac   576 aagatggata cctttttttgc gaaatcgttg ccagagtttg ttttctgaga tgatttaga   636 ctagtacaca ctctttattt acccagaagg tattctgaat caatgttctt tttgttgtta   696 ttattgtatt tcatagcttt gaaacttaaa aaaaaaaaa aaaaaaaa                 744
```

<210> SEQ ID NO 6

<211> LENGTH: 102
<212> TYPE: PRT
<213> ORGANISM: Lycopersicon esculentum

<400> SEQUENCE: 6

```
Ile Arg His Glu Ala Asp Leu Thr Gly Glu Leu Met Arg Leu Ala Ile
  1               5                  10                  15

Gly Arg Ile Ser Glu Gly Glu Leu Asp Phe Ala Glu Lys Ile Cys Ser
             20                  25                  30

Phe Ala Arg Glu Ile Tyr Arg Asn Leu Thr Leu Ile Ala Pro Glu Met
         35                  40                  45

Asp Asp Ser Ser Asp Met Lys Gln Lys Met Glu Thr Met Leu Gln Ser
 50                  55                  60

Val Met Lys Ile Glu Asn Ala Cys Phe Ser Val His Val Arg Gly Ser
 65                  70                  75                  80

Glu Tyr Ile Pro Leu Leu Gly Pro Ala Asp Thr Ser Tyr Pro Leu Leu
                 85                  90                  95

Gly Met Pro Asp Ile Glu
            100
```

<210> SEQ ID NO 7
<211> LENGTH: 296
<212> TYPE: DNA
<213> ORGANISM: Lycopersicon esculentum
<220> FEATURE:
<221> NAME/KEY: CDS
<222> LOCATION: (52)..(294)
<220> FEATURE:
<221> NAME/KEY: misc_feature
<222> LOCATION: Complement((1)..(296))
<223> OTHER INFORMATION: Interactor J-49 (Hsp17)

<400> SEQUENCE: 7

```
cgaattcggc acgagaaaaa acgtagaaaa ttctcaaaaa gttcactgaa a atg tct     57
                                                         Met Ser
                                                           1 ctg atc cca aga att ttc ggc gat cga cga agc agc agc atg ttc gat    105
Leu Ile Pro Arg Ile Phe Gly Asp Arg Arg Ser Ser Ser Met Phe Asp
      5                  10                  15 cca ttt tca att gac gta ttt gat cca ttc agg gaa tta ggc ttc cca    153
Pro Phe Ser Ile Asp Val Phe Asp Pro Phe Arg Glu Leu Gly Phe Pro
 20                  25                  30 agt acc aat tca ggg gag agc tct gca ttt gcc aac aca cga ata gac    201
Ser Thr Asn Ser Gly Glu Ser Ser Ala Phe Ala Asn Thr Arg Ile Asp
 35                  40                  45                  50 tgg aag gaa act cca gaa gct cat gtg ttc aag gtt gat ctt cca ggg    249
Trp Lys Glu Thr Pro Glu Ala His Val Phe Lys Val Asp Leu Pro Gly
             55                  60                  65 ctt aag aag gag gaa gtc aaa gtg gaa gtc gag gag gaa ata ggg gt     296
Leu Lys Lys Glu Glu Val Lys Val Glu Val Glu Glu Glu Ile Gly
     70                  75                  80
```

<210> SEQ ID NO 8
<211> LENGTH: 81
<212> TYPE: PRT
<213> ORGANISM: Lycopersicon esculentum

<400> SEQUENCE: 8

```
Met Ser Leu Ile Pro Arg Ile Phe Gly Asp Arg Arg Ser Ser Ser Met
  1               5                  10                  15

Phe Asp Pro Phe Ser Ile Asp Val Phe Asp Pro Phe Arg Glu Leu Gly
             20                  25                  30
```

-continued

```
Phe Pro Ser Thr Asn Ser Gly Glu Ser Ser Ala Phe Ala Asn Thr Arg
        35                  40                  45

Ile Asp Trp Lys Glu Thr Pro Glu Ala His Val Phe Lys Val Asp Leu
 50                  55                  60

Pro Gly Leu Lys Lys Glu Val Lys Val Glu Val Glu Glu Ile
 65                  70                  75                  80

Gly

<210> SEQ ID NO 9
<211> LENGTH: 1885
<212> TYPE: DNA
<213> ORGANISM: Lycopersicon esculentum
<220> FEATURE:
<221> NAME/KEY: CDS
<222> LOCATION: (55)..(1509)
<220> FEATURE:
<221> NAME/KEY: misc_feature
<222> LOCATION: Complement((1)..(1885))
<223> OTHER INFORMATION: Interactor S-25 (PP5, TPR-Phosphatase)

<400> SEQUENCE: 9
```

| | | |
|---|---|---|
| tgaattcggc acgagacgca acatctactc agccagcctc cagtcgccat tgtt atg | | 57 |
| | Met | |
| | 1 | |

| | | |
|---|---|---|
| ccc ggt atg gaa gct gag aac tca aac gcc tcc cga gct gaa gaa ctc | | 105 |
| Pro Gly Met Glu Ala Glu Asn Ser Asn Ala Ser Arg Ala Glu Glu Leu | | |
| 5 10 15 | | |

| | | |
|---|---|---|
| aag caa ctc gca aat gaa gca ttc aaa ggg cat aag tat tcg caa gct | | 153 |
| Lys Gln Leu Ala Asn Glu Ala Phe Lys Gly His Lys Tyr Ser Gln Ala | | |
| 20 25 30 | | |

| | | |
|---|---|---|
| att gat ctg tac aca caa gcg att gag ttg aac ggt gag aat gcg gtg | | 201 |
| Ile Asp Leu Tyr Thr Gln Ala Ile Glu Leu Asn Gly Glu Asn Ala Val | | |
| 35 40 45 | | |

| | | |
|---|---|---|
| tac tat gct aac cgt gcg ttt gct cac acc aaa ttg gag gaa tat gga | | 249 |
| Tyr Tyr Ala Asn Arg Ala Phe Ala His Thr Lys Leu Glu Glu Tyr Gly | | |
| 50 55 60 65 | | |

| | | |
|---|---|---|
| agc gca ata cag gat gga act aga gct att gaa att gac cct aga tat | | 297 |
| Ser Ala Ile Gln Asp Gly Thr Arg Ala Ile Glu Ile Asp Pro Arg Tyr | | |
| 70 75 80 | | |

| | | |
|---|---|---|
| tca aag ggt tat tat agg aga gga gct gca tat ttg gca atg ggg aag | | 345 |
| Ser Lys Gly Tyr Tyr Arg Arg Gly Ala Ala Tyr Leu Ala Met Gly Lys | | |
| 85 90 95 | | |

| | | |
|---|---|---|
| ttc aaa gat gca ctc aag gat ttt caa cag gtc aag aaa tta tgt cca | | 393 |
| Phe Lys Asp Ala Leu Lys Asp Phe Gln Gln Val Lys Lys Leu Cys Pro | | |
| 100 105 110 | | |

| | | |
|---|---|---|
| aac gac cca gat gct acc aaa aaa ttg aag gaa tgt gag aaa gct gtc | | 441 |
| Asn Asp Pro Asp Ala Thr Lys Lys Leu Lys Glu Cys Glu Lys Ala Val | | |
| 115 120 125 | | |

| | | |
|---|---|---|
| atg aag cta aaa ttt gaa gaa gct att tct gtc cca gaa tct cag agg | | 489 |
| Met Lys Leu Lys Phe Glu Glu Ala Ile Ser Val Pro Glu Ser Gln Arg | | |
| 130 135 140 145 | | |

| | | |
|---|---|---|
| cgt tca gta gct gac tct att gat tat cgt tct gta gag gtg gag cct | | 537 |
| Arg Ser Val Ala Asp Ser Ile Asp Tyr Arg Ser Val Glu Val Glu Pro | | |
| 150 155 160 | | |

| | | |
|---|---|---|
| caa tat gct ggt gca aga ata gag gga gat gtt gta aca tta gat ttt | | 585 |
| Gln Tyr Ala Gly Ala Arg Ile Glu Gly Asp Val Val Thr Leu Asp Phe | | |
| 165 170 175 | | |

| | | |
|---|---|---|
| gtg aag aag atg ctg gat gac ttc aaa aac cag aag aac ttg cat aag | | 633 |
| Val Lys Lys Met Leu Asp Asp Phe Lys Asn Gln Lys Asn Leu His Lys | | |
| 180 185 190 | | |

-continued

| | | |
|---|---|---|
| agg tat gcc tac caa ata gta ctg caa aca aga gaa atg ttg cga gca<br>Arg Tyr Ala Tyr Gln Ile Val Leu Gln Thr Arg Glu Met Leu Arg Ala<br>195                       200                     205 | 681 |
| ctg ccc tcc ctt gtt gac att gtt gtt ccc gaa ggg aag cac ttc act<br>Leu Pro Ser Leu Val Asp Ile Val Val Pro Glu Gly Lys His Phe Thr<br>210                     215                     220                 225 | 729 |
| gta tgt ggt gat gta cat ggt cag ttt tat gac ctc cta aat att ttc<br>Val Cys Gly Asp Val His Gly Gln Phe Tyr Asp Leu Leu Asn Ile Phe<br>                   230                     235                 240 | 777 |
| gag ctc aat ggg ctt cca tca gaa gac aat ccg tat ctg ttc aat ggt<br>Glu Leu Asn Gly Leu Pro Ser Glu Asp Asn Pro Tyr Leu Phe Asn Gly<br>245                     250                     255 | 825 |
| gat ttt gtt gat aga ggg tct ttc tct cta gag gtc ata ttg aca tta<br>Asp Phe Val Asp Arg Gly Ser Phe Ser Leu Glu Val Ile Leu Thr Leu<br>             260                     265                 270 | 873 |
| ttt gcc ttc aag tgc atg tgt cca tca gct ata cac ctg gcg aga gga<br>Phe Ala Phe Lys Cys Met Cys Pro Ser Ala Ile His Leu Ala Arg Gly<br>275                     280                     285 | 921 |
| aat cac gaa agc aag agc atg aac aaa ata tat ggg ttt gag ggc gag<br>Asn His Glu Ser Lys Ser Met Asn Lys Ile Tyr Gly Phe Glu Gly Glu<br>290                     295                     300                 305 | 969 |
| gtc aga tcc aag tta agt gaa ata ttt gtg gaa ctc ttt gca gaa gtg<br>Val Arg Ser Lys Leu Ser Glu Ile Phe Val Glu Leu Phe Ala Glu Val<br>             310                     315                 320 | 1017 |
| ttc tgt tgc tta cct ttg gcc cat gtc ata aat gag aaa gtc ttt gta<br>Phe Cys Cys Leu Pro Leu Ala His Val Ile Asn Glu Lys Val Phe Val<br>                   325                     330                 335 | 1065 |
| gta cat aga ggt ctt ttt agt gtt gat ggc gtg aag ctc tct gat att<br>Val His Arg Gly Leu Phe Ser Val Asp Gly Val Lys Leu Ser Asp Ile<br>340                     345                     350 | 1113 |
| aga gca att gat cgg ttt tgt gag ccc cca gaa gag ggg tta atg tgt<br>Arg Ala Ile Asp Arg Phe Cys Glu Pro Pro Glu Glu Gly Leu Met Cys<br>355                     360                     365 | 1161 |
| gaa ttg ttg tgg agt gat cca caa cct cag cct ggt aga gga cct agt<br>Glu Leu Leu Trp Ser Asp Pro Gln Pro Gln Pro Gly Arg Gly Pro Ser<br>370                     375                     380                 385 | 1209 |
| aaa cga ggt gtt ggt ctt tct ttc ggg gga gac gta act aaa aga ttc<br>Lys Arg Gly Val Gly Leu Ser Phe Gly Gly Asp Val Thr Lys Arg Phe<br>             390                     395                 400 | 1257 |
| ttg cag gaa aat aat cta gat tta gtg gtg cga tct cat gaa gtg aag<br>Leu Gln Glu Asn Asn Leu Asp Leu Val Val Arg Ser His Glu Val Lys<br>                   405                     410                 415 | 1305 |
| gat gaa ggt tat gag att gag cat gac ggc aaa ctc ata acg gtg ttt<br>Asp Glu Gly Tyr Glu Ile Glu His Asp Gly Lys Leu Ile Thr Val Phe<br>420                     425                     430 | 1353 |
| tcc gct ccc aat tat tgt gac cag atg ggt aac aag ggt gct ttt ata<br>Ser Ala Pro Asn Tyr Cys Asp Gln Met Gly Asn Lys Gly Ala Phe Ile<br>435                     440                     445 | 1401 |
| cga ttt gag gct ccc gat atg aag cca aat att gtg aca ttt tca gca<br>Arg Phe Glu Ala Pro Asp Met Lys Pro Asn Ile Val Thr Phe Ser Ala<br>450                     455                     460                 465 | 1449 |
| gtg cca cat cct gat gtc aaa cca atg gca tat gcc aac aac ttc ctt<br>Val Pro His Pro Asp Val Lys Pro Met Ala Tyr Ala Asn Asn Phe Leu<br>             470                     475                 480 | 1497 |
| cgc atg ttt tct taaaaactct ggaacctaac gttcagtatt acaatcgatg<br>Arg Met Phe Ser<br>485 | 1549 |
| cgaccttttg tctgactgac caagagcata cacatcagga ggcaaaagag ctagtactta | 1609 |
| cagccaatta gctgcagtgt cattattcgg acaacttcct gacttgcccg cagcatgtga | 1669 |

-continued

```
ggatcctcac ctcctttgtt ttgattaagg cgtaaacact ttctctacga taacaatgtc   1729
gtgtggtgga ttgtcctctg tattatttat attcctcttt gtaagattgt tacacttctc   1789
atttctttta gaatgttcaa attgggaaaa gctttgataa gtcgaatttt ggtttttct    1849 aaaaaaaaaa aaaaaaaaa aaaaaaaaa aaaaaa                                1885
```

<210> SEQ ID NO 10
<211> LENGTH: 485
<212> TYPE: PRT
<213> ORGANISM: Lycopersicon esculentum

<400> SEQUENCE: 10

```
Met Pro Gly Met Glu Ala Glu Asn Ser Asn Ala Ser Arg Ala Glu Glu
 1               5                  10                  15

Leu Lys Gln Leu Ala Asn Glu Ala Phe Lys Gly His Lys Tyr Ser Gln
                20                  25                  30

Ala Ile Asp Leu Tyr Thr Gln Ala Ile Glu Leu Asn Gly Glu Asn Ala
            35                  40                  45

Val Tyr Tyr Ala Asn Arg Ala Phe Ala His Thr Lys Leu Glu Glu Tyr
        50                  55                  60

Gly Ser Ala Ile Gln Asp Gly Thr Arg Ala Ile Glu Ile Asp Pro Arg
 65                  70                  75                  80

Tyr Ser Lys Gly Tyr Tyr Arg Arg Gly Ala Ala Tyr Leu Ala Met Gly
                 85                  90                  95

Lys Phe Lys Asp Ala Leu Lys Asp Phe Gln Gln Val Lys Lys Leu Cys
            100                 105                 110

Pro Asn Asp Pro Asp Ala Thr Lys Lys Leu Lys Glu Cys Glu Lys Ala
        115                 120                 125

Val Met Lys Leu Lys Phe Glu Glu Ala Ile Ser Val Pro Glu Ser Gln
    130                 135                 140

Arg Arg Ser Val Ala Asp Ser Ile Asp Tyr Arg Ser Val Glu Val Glu
145                 150                 155                 160

Pro Gln Tyr Ala Gly Ala Arg Ile Glu Gly Asp Val Val Thr Leu Asp
                165                 170                 175

Phe Val Lys Lys Met Leu Asp Asp Phe Lys Asn Gln Lys Asn Leu His
            180                 185                 190

Lys Arg Tyr Ala Tyr Gln Ile Val Leu Gln Thr Arg Glu Met Leu Arg
        195                 200                 205

Ala Leu Pro Ser Leu Val Asp Ile Val Val Pro Glu Gly Lys His Phe
    210                 215                 220

Thr Val Cys Gly Asp Val His Gly Gln Phe Tyr Asp Leu Leu Asn Ile
225                 230                 235                 240

Phe Glu Leu Asn Gly Leu Pro Ser Glu Asp Asn Pro Tyr Leu Phe Asn
                245                 250                 255

Gly Asp Phe Val Asp Arg Gly Ser Phe Ser Leu Glu Val Ile Leu Thr
            260                 265                 270

Leu Phe Ala Phe Lys Cys Met Cys Pro Ser Ala Ile His Leu Ala Arg
        275                 280                 285

Gly Asn His Glu Ser Lys Ser Met Asn Lys Ile Tyr Gly Phe Glu Gly
    290                 295                 300

Glu Val Arg Ser Lys Leu Ser Glu Ile Phe Val Glu Leu Phe Ala Glu
305                 310                 315                 320

Val Phe Cys Cys Leu Pro Leu Ala His Val Ile Asn Glu Lys Val Phe
                325                 330                 335
```

```
Val Val His Arg Gly Leu Phe Ser Val Asp Gly Val Lys Leu Ser Asp
            340                 345                 350

Ile Arg Ala Ile Asp Arg Phe Cys Glu Pro Pro Glu Gly Leu Met
            355                 360                 365

Cys Glu Leu Leu Trp Ser Asp Pro Gln Pro Gln Pro Gly Arg Gly Pro
            370                 375                 380

Ser Lys Arg Gly Val Gly Leu Ser Phe Gly Gly Asp Val Thr Lys Arg
385                 390                 395                 400

Phe Leu Gln Glu Asn Asn Leu Asp Leu Val Val Arg Ser His Glu Val
                    405                 410                 415

Lys Asp Glu Gly Tyr Glu Ile Glu His Asp Gly Lys Leu Ile Thr Val
                    420                 425                 430

Phe Ser Ala Pro Asn Tyr Cys Asp Gln Met Gly Asn Lys Gly Ala Phe
                    435                 440                 445

Ile Arg Phe Glu Ala Pro Asp Met Lys Pro Asn Ile Val Thr Phe Ser
            450                 455                 460

Ala Val Pro His Pro Asp Val Lys Pro Met Ala Tyr Ala Asn Asn Phe
465                 470                 475                 480

Leu Arg Met Phe Ser
                485

<210> SEQ ID NO 11
<211> LENGTH: 153
<212> TYPE: PRT
<213> ORGANISM: Lycopersicon esculentum

<400> SEQUENCE: 11

Met Ser Leu Ile Pro Ser Ile Phe Gly Gly Arg Arg Ser Asn Val Phe
1               5                   10                  15

Asp Pro Phe Ser Leu Asp Val Trp Asp Pro Phe Lys Asp Phe His Phe
                20                  25                  30

Pro Thr Ser Leu Ser Ala Glu Asn Ser Ala Phe Val Asn Thr Arg Val
            35                  40                  45

Asp Trp Lys Glu Thr Pro Glu Ala His Val Phe Glu Ala Asp Ile Pro
    50                  55                  60

Gly Leu Lys Lys Glu Glu Val Lys Val Gln Ile Glu Asp Asp Arg Val
65                  70                  75                  80

Leu Gln Ile Ser Gly Glu Arg Asn Leu Glu Lys Glu Asp Lys Asn Asp
                85                  90                  95

Thr Trp His Arg Val Glu Arg Ser Ser Gly Asn Phe Met Arg Arg Phe
            100                 105                 110

Arg Leu Pro Glu Asn Ala Lys Val Glu Gln Val Lys Ala Ser Met Glu
        115                 120                 125

Asn Gly Val Leu Thr Val Thr Val Pro Lys Glu Glu Val Lys Lys Pro
    130                 135                 140

Asp Val Lys Ala Ile Glu Ile Ser Gly
145                 150

<210> SEQ ID NO 12
<211> LENGTH: 153
<212> TYPE: PRT
<213> ORGANISM: Lycopersicon esculentum

<400> SEQUENCE: 12

Met Ser Met Ile Pro Ser Phe Phe Asn Asn Asn Arg Arg Ser Asn Ile
1               5                   10                  15
```

Phe Asp Pro Phe Ser Leu Asp Val Trp Asp Pro Phe Lys Glu Leu Thr
                20                  25                  30

Ser Ser Ser Leu Ser Arg Glu Asn Ser Ala Ile Val Asn Ala Arg Val
        35                  40                  45

Asp Trp Arg Glu Thr Pro Glu Ala His Val Phe Lys Ala Asp Leu Pro
    50                  55                  60

Gly Leu Lys Lys Glu Glu Val Lys Val Glu Ile Glu Glu Asp Ser Val
65                  70                  75                  80

Leu Lys Ile Ser Gly Glu Arg His Val Glu Lys Glu Asp Lys Asn Asp
                85                  90                  95

Thr Trp His Arg Val Glu Arg Ser Ser Gly Gln Phe Thr Arg Arg Phe
            100                 105                 110

Arg Leu Pro Glu Asn Val Lys Met Asp Gln Val Lys Ala Ala Met Glu
        115                 120                 125

Asn Gly Val Leu Thr Val Thr Val Pro Lys Ala Glu Thr Lys Lys Ala
    130                 135                 140

Asp Val Lys Ser Ile Gln Ile Ser Gly
145                 150

<210> SEQ ID NO 13
<211> LENGTH: 151
<212> TYPE: PRT
<213> ORGANISM: Lycopersicon esculentum

<400> SEQUENCE: 13

Met Ser Ile Val Arg Arg Ser Asn Val Phe Asp Pro Phe Ala Asp Leu
1               5                   10                  15

Trp Ala Asp Pro Phe Asp Thr Phe Arg Ser Ile Val Pro Ala Ile Ser
                20                  25                  30

Gly Gly Ser Ser Glu Thr Ala Ala Phe Ala Asn Ala Arg Val Asp Trp
            35                  40                  45

Lys Glu Thr Pro Glu Ala His Val Phe Lys Val Asp Leu Pro Gly Val
    50                  55                  60

Lys Lys Glu Glu Val Lys Val Glu Val Glu Asp Gly Asn Val Leu Val
65                  70                  75                  80

Val Ser Gly Glu Arg Ser Arg Glu Lys Glu Asp Lys Asn Asp Lys Trp
                85                  90                  95

His Arg Val Glu Arg Ser Ser Gly Lys Phe Val Arg Arg Phe Arg Leu
            100                 105                 110

Pro Glu Asp Ala Lys Val Glu Glu Val Lys Ala Gly Leu Glu Asn Gly
        115                 120                 125

Val Leu Thr Val Thr Val Pro Lys Ala Glu Val Lys Lys Pro Glu Val
    130                 135                 140

Lys Ala Ile Glu Ile Ser Gly
145                 150

<210> SEQ ID NO 14
<211> LENGTH: 152
<212> TYPE: PRT
<213> ORGANISM: Lycopersicon esculentum

<400> SEQUENCE: 14

Met Ser Leu Val Arg Arg Ser Asn Val Phe Asp Pro Phe Ser Met Asp
1               5                   10                  15

Leu Trp Asp Pro Phe Asp Thr Met Phe Arg Ser Ile Val Pro Ser Ala
                20                  25                  30

Thr Ser Thr Asn Ser Glu Thr Ala Ala Phe Ala Ser Ala Arg Ile Asp
         35                  40                  45

Trp Lys Glu Thr Pro Glu Ala His Val Phe Lys Ala Asp Leu Pro Gly
 50                  55                  60

Val Lys Lys Glu Glu Val Lys Val Glu Val Glu Asp Gly Asn Val Leu
 65                  70                  75                  80

Val Ile Ser Gly Gln Arg Ser Arg Glu Lys Asp Lys Asp Lys
                 85                  90                  95

Trp His Arg Val Glu Arg Ser Ser Gly Gln Phe Ile Arg Arg Phe Arg
                100                 105                 110

Leu Pro Asp Asp Ala Lys Val Asp Gln Val Lys Ala Gly Leu Glu Asn
             115                 120                 125

Gly Val Leu Thr Val Thr Val Pro Lys Ala Glu Glu Lys Lys Pro Glu
         130                 135                 140

Val Lys Ala Ile Glu Ile Ser Gly
145                 150

<210> SEQ ID NO 15
<211> LENGTH: 217
<212> TYPE: PRT
<213> ORGANISM: Lycopersicon esculentum

<400> SEQUENCE: 15

Ile Arg His Glu Ala Ala Arg Lys Leu Arg Glu Asn Gln Ser Thr Thr
  1               5                  10                  15

Ser Val Gln Thr Glu Asp Leu Val Glu Asp Pro Ala Gln Glu Ser Ala
                 20                  25                  30

Asp Tyr His Arg Asn Leu Gly Leu Gln Met Val Ser Gly Leu Ser Asn
             35                  40                  45

Glu Leu Glu Asn Val Arg Lys Ala Ser Leu Ile Asp Gly Glu Asn Leu
         50                  55                  60

Ser Ala Ala Val Met Lys Leu Asn His Ser Leu Met Lys Thr Lys Glu
 65                  70                  75                  80

Phe Leu Asp Thr Asp Met Arg Ser Leu Glu Asp Glu Ser Lys Phe Arg
                 85                  90                  95

Asp Thr Leu Thr Asn Phe Ile Gln His Ala Glu Gln Asp Ile Thr Cys
            100                 105                 110

Ile Leu Glu Glu Glu Lys Lys Ile Met Ser Leu Val Lys Ser Thr Gly
        115                 120                 125

Asp Tyr Phe His Gly Asn Ser Gly Lys Asp Glu Gly Leu Arg Leu Phe
    130                 135                 140

Ser Val Val Ser Asp Phe Leu Ile Met Leu Asp Lys Ala Cys Thr Val
145                 150                 155                 160

Val Arg Asn Ser Thr Lys Leu Pro Val Lys Ile Pro Lys Lys Gly Thr
                165                 170                 175

Leu Thr Ser Pro Ser Gln Glu Ser Cys Pro Glu Ser Leu Gln Asp Ile
            180                 185                 190

Arg Lys Gln Leu Phe Pro Ala Ile Gln Glu Arg Gln Met His Tyr Ser
        195                 200                 205

Ser Ser Asp Asp Glu Ser Ser Pro
    210                 215

<210> SEQ ID NO 16
<211> LENGTH: 256
<212> TYPE: PRT

-continued

<213> ORGANISM: Arabidopsis arenosa

<400> SEQUENCE: 16

```
Arg Met Asn Val Gly Thr Phe Arg Gly Asp Ala Gln Ala Phe Lys Leu
  1               5                  10                  15

Asp Thr Leu Leu Lys Leu Ser Asp Val Lys Gly Thr Asp Gly Lys Thr
             20                  25                  30

Thr Leu Leu His Phe Val Val Leu Glu Ile Ile Arg Ser Glu Gly Val
         35                  40                  45

Arg Ala Leu Arg Leu Gln Ser Arg Ser Phe Ser Ser Val Lys Thr Asp
     50                  55                  60

Asp Ser Asn Ala Asp Ser Ser Pro Gln Ser Val Asp Tyr Arg Ser Thr
 65                  70                  75                  80

Gly Leu Gln Val Val Thr Gly Leu Thr Thr Glu Leu Glu Asp Val Lys
                 85                  90                  95

Arg Ala Ala Ile Ile Asp Ala Asp Gly Leu Ala Ala Thr Leu Ala Asn
            100                 105                 110

Ile Ser Gly Ser Leu Thr Asn Ala Arg Glu Phe Leu Lys Thr Met Asp
        115                 120                 125

Glu Glu Ser Asp Phe Glu Arg Ala Leu Ala Gly Phe Ile Glu Arg Ala
    130                 135                 140

Asp Ala Asp Phe Lys Trp Leu Lys Glu Glu Glu Arg Ile Met Val
145                 150                 155                 160

Leu Val Lys Ser Ser Ala Asp Tyr Phe His Gly Lys Ser Ala Lys Asn
                165                 170                 175

Glu Gly Leu Arg Leu Phe Ala Ile Val Arg Asp Phe Leu Ile Met Leu
            180                 185                 190

Glu Lys Val Cys Arg Glu Val Lys Glu Thr Thr Lys Thr Thr Asn His
        195                 200                 205

Ser Gly Lys Lys Glu Ser Glu Met Thr Thr Ser Asp Ser Asn Gln Pro
    210                 215                 220

Ser Pro Asp Phe Arg Gln Arg Leu Phe Pro Ala Ile Ala Glu Arg Arg
225                 230                 235                 240

Met Asp Ser Ser Asp Asp Ser Asp Ser Glu Glu Asp Ser Ser Pro
                245                 250                 255
```

<210> SEQ ID NO 17
<211> LENGTH: 242
<212> TYPE: PRT
<213> ORGANISM: Arabidopsis thaliana

<400> SEQUENCE: 17

```
Arg Met Asn Val Gly Thr Asn Arg Gly Asp Ala His Ala Phe Lys Leu
  1               5                  10                  15

Asp Thr Leu Leu Lys Leu Val Asp Val Lys Gly Ala Asp Gly Lys Thr
             20                  25                  30

Thr Leu Leu His Phe Val Val Gln Glu Ile Ile Arg Ala Glu Gly Thr
         35                  40                  45

Arg Leu Ser Gly Asn Asn Thr Gln Thr Asp Asp Ile Lys Cys Arg Lys
     50                  55                  60

Leu Gly Leu Gln Val Val Ser Ser Leu Cys Ser Glu Leu Ser Asn Val
 65                  70                  75                  80

Lys Lys Ala Ala Ala Met Asp Ser Glu Val Leu Ser Ser Tyr Val Ser
                 85                  90                  95

Lys Leu Ser Gln Gly Ile Ala Lys Ile Asn Glu Ala Ile Gln Val Gln
```

-continued

```
              100                 105                 110
Ser Thr Ile Thr Glu Glu Ser Asn Ser Gln Arg Phe Ser Glu Ser Met
            115                 120                 125
Lys Thr Phe Leu Lys Arg Ala Glu Glu Ile Ile Arg Val Gln Ala
130                 135                 140
Gln Glu Ser Val Ala Leu Ser Leu Val Lys Glu Ile Thr Glu Tyr Phe
145                 150                 155                 160
His Gly Asn Ser Ala Lys Glu Ala His Pro Phe Arg Ile Phe Leu
                165                 170                 175
Val Val Arg Asp Phe Leu Gly Val Val Asp Arg Val Cys Lys Glu Val
            180                 185                 190
Gly Met Ile Asn Glu Arg Thr Met Val Ser Ser Ala His Lys Phe Pro
            195                 200                 205
Val Pro Val Asn Pro Met Met Pro Gln Pro Leu Pro Gly Leu Val Gly
            210                 215                 220
Arg Arg Gln Ser Ser Ser Ser Ser Ser Ser Thr Ser Ser Ser
225                 230                 235                 240
Asp Glu

<210> SEQ ID NO 18
<211> LENGTH: 245
<212> TYPE: PRT
<213> ORGANISM: Nicotiana tabacum

<400> SEQUENCE: 18

Arg Met Asn Val Gly Thr Asn Arg Gly Asp Ala His Ala Phe Lys Leu
1               5                   10                  15
Asp Thr Leu Leu Lys Leu Val Asp Val Lys Gly Ala Asp Gly Lys Thr
            20                  25                  30
Thr Leu Leu His Phe Val Val Gln Glu Ile Ile Lys Ser Glu Gly Ala
        35                  40                  45
Arg Leu Ser Gly Gly Asn Gln Asn His Gln Gln Ser Thr Thr Asn Asp
    50                  55                  60
Asp Ala Lys Cys Lys Lys Leu Gly Leu Gln Val Val Ser Asn Ile Ser
65                  70                  75                  80
Ser Glu Leu Ile Asn Val Lys Lys Ser Ala Ala Met Asp Ser Glu Val
                85                  90                  95
Leu His Asn Asp Val Leu Lys Leu Ser Lys Gly Ile Gln Asn Ile Ala
            100                 105                 110
Glu Val Val Arg Ser Ile Glu Ala Val Gly Leu Glu Glu Ser Ser Ile
        115                 120                 125
Lys Arg Phe Ser Glu Ser Met Asn Arg Phe Met Lys Val Ala Glu Glu
    130                 135                 140
Lys Ile Leu Arg Leu Gln Ala Gln Glu Thr Leu Ala Met Ser Leu Val
145                 150                 155                 160
Lys Glu Ile Thr Glu Tyr Val His Gly Asp Ser Ala Arg Glu Glu Ala
                165                 170                 175
His Pro Phe Arg Ile Phe Met Val Val Lys Asp Phe Leu Met Ile Leu
            180                 185                 190
Asp Cys Val Cys Lys Glu Val Gly Thr Ile Asn Glu Arg Thr Ile Val
        195                 200                 205
Ser Ser Ala Gln Lys Phe Pro Val Pro Val Asn Pro Asn Leu Gln Pro
    210                 215                 220
Val Ile Ser Gly Phe Arg Ala Lys Arg Leu His Ser Ser Ser Asp Glu
```

```
                     225                 230                 235                 240

Glu Ser Ser Ser Pro
                        245

<210> SEQ ID NO 19
<211> LENGTH: 117
<212> TYPE: PRT
<213> ORGANISM: Picea mariana

<400> SEQUENCE: 19

Gln Gly Asn Phe Phe Lys Ser Met Ser Ser Phe Leu Gln Glu Ala Glu
          1               5                  10                  15

Glu Asp Ile Ala Arg Ile Gln Ser Glu Glu Asn Arg Ala Phe Ser Leu
                         20                  25                  30

Val Arg Glu Thr Thr Glu Tyr Phe His Gly Asp Ala Ala Lys Glu Glu
                     35                  40                  45

Gly Arg Pro Leu Arg Phe Phe Val Val Lys Asp Phe Leu Gly Val
             50                  55                  60

Leu Asp Gln Val Cys Arg Glu Ile Gly Lys Thr Arg Thr Arg Met Ala
         65                  70                  75                  80

Gln Ser Ser Pro Arg Pro Pro Gln Val Ala His Ala Ile Ser Met
                         85                  90                  95

Pro Leu Phe Pro Lys Ala Leu Gln Arg Arg Pro Asp Ser Ser Asp Asp
                        100                 105                 110

Glu Ser Ser Ser Pro
                    115

<210> SEQ ID NO 20
<211> LENGTH: 180
<212> TYPE: PRT
<213> ORGANISM: Arabidopsis thaliana

<400> SEQUENCE: 20

Met Lys Ser Gly Asn Ala His Asp Phe Lys Leu Glu Ala Leu Leu Gly
          1               5                  10                  15

Leu Val Asp Ile Lys Ser Ser Asp Gly Arg Thr Ser Ile Leu Asp Ser
                         20                  25                  30

Val Val Gln Lys Ile Thr Glu Ser Glu Gly Ile Lys Gly Leu Gln Val
                     35                  40                  45

Val Arg Asn Leu Ser Ser Val Leu Asn Asp Ala Lys Lys Ser Ala Glu
             50                  55                  60

Leu Asp Tyr Gly Val Val Arg Met Asn Val Ser Lys Leu Tyr Glu Glu
         65                  70                  75                  80

Val Gln Lys Ile Ser Glu Val Leu Arg Leu Cys Glu Glu Thr Gly His
                         85                  90                  95

Ser Glu Glu His Gln Trp Trp Lys Phe Arg Glu Ser Val Thr Arg Phe
                        100                 105                 110

Leu Glu Thr Ala Ala Glu Glu Ile Lys Lys Ile Glu Arg Glu Glu Gly
                    115                 120                 125

Ser Thr Leu Phe Ala Val Lys Lys Ile Thr Glu Tyr Phe His Val Asp
                130                 135                 140

Pro Ala Lys Glu Glu Ala Gln Leu Leu Lys Val Phe Ile Val Arg
        145                 150                 155                 160

Asp Phe Leu Lys Ile Leu Glu Gly Val Cys Lys Lys Met Glu Val Thr
                        165                 170                 175

Ser Ser Leu Ala
```

180

<210> SEQ ID NO 21
<211> LENGTH: 98
<212> TYPE: PRT
<213> ORGANISM: Lycopersicon esculentum

<400> SEQUENCE: 21

Ala Asp Leu Thr Gly Glu Leu Met Arg Leu Ala Ile Gly Arg Ile Ser
 1               5                  10                  15

Glu Gly Glu Leu Asp Phe Ala Glu Lys Ile Cys Ser Phe Ala Arg Glu
            20                  25                  30

Ile Tyr Arg Asn Leu Thr Leu Ile Ala Pro Glu Met Asp Asp Ser Ser
        35                  40                  45

Asp Met Lys Gln Lys Met Glu Thr Met Leu Gln Ser Val Met Lys Ile
    50                  55                  60

Glu Asn Ala Cys Phe Ser Val His Val Arg Gly Ser Glu Tyr Ile Pro
 65                  70                  75                  80

Leu Leu Gly Pro Ala Asp Thr Ser Tyr Pro Leu Leu Gly Met Pro Asp
                85                  90                  95

Ile Glu

<210> SEQ ID NO 22
<211> LENGTH: 299
<212> TYPE: PRT
<213> ORGANISM: Arabidopsis thaliana

<400> SEQUENCE: 22

Met Leu Ser Cys Ser Ser Ser Ala Phe Gln Arg Val Ala Phe Met Leu
 1               5                  10                  15

Met Ala Pro Lys Leu Lys Pro Gln Arg Leu His Gln Met Leu Ile Ser
            20                  25                  30

Asn Asp Gly Phe Gly Val Cys Val Ala Glu Ser Gly Val Glu His
        35                  40                  45

Leu Val Lys Lys Ala Arg Thr Met Ser Thr Glu Ser Ser Met Lys Asp
    50                  55                  60

Ala Phe Ser Thr Tyr Ala Asp Tyr Leu Asn Asn Phe Asn Glu Lys Arg
 65                  70                  75                  80

Glu Arg Val Val Lys Val Ser Arg Asp Ile Thr Met Asn Ser Lys Lys
                85                  90                  95

Val Ile Phe Gln Val His Arg Leu Ser Lys Asp Asn Lys Glu Glu Val
            100                 105                 110

Leu Glu Lys Ala Gly Lys Asp Leu Glu Ala Val Arg Asp Gln His Phe
        115                 120                 125

Ala Arg Leu Met Lys Glu Leu Gln Gly Thr Asp Phe Trp Lys Leu Arg
    130                 135                 140

Arg Ala Tyr Ser Pro Gly Val Gln Glu Tyr Val Glu Ala Ala Thr Phe
145                 150                 155                 160

Tyr Lys Phe Cys Leu Ser Gly Thr Leu Cys Thr Leu Asp Glu Ile Asn
                165                 170                 175

Thr Thr Leu Val Pro Leu Ser Asp Pro Ser Leu Glu Pro Leu Gln Ile
            180                 185                 190

Asn Ile Leu Asp Tyr Ile Leu Gly Leu Ala Asp Leu Thr Gly Glu Leu
        195                 200                 205

Met Arg Met Ala Ile Gly Arg Ile Ser Asp Gly Glu Ile Glu Phe Ala
    210                 215                 220

```
Gln Arg Ile Cys Gln Phe Val Arg Gln Ile His Arg Glu Leu Met Leu
225                 230                 235                 240

Val Val Pro Lys Met Asp Asp Ser Tyr Asp Met Lys Ser Lys Met Glu
            245                 250                 255

Val Met Leu Gln Ser Val Ile Lys Ile Glu Asn Ala Cys Phe Ser Val
            260                 265                 270

His Val Arg Gly Leu Glu Tyr Ile Pro Leu Leu Gly Asp Asn Ala Pro
        275                 280                 285

Thr Ser Tyr Leu Leu Gly Ala Ala Asp Val Glu
    290                 295

<210> SEQ ID NO 23
<211> LENGTH: 300
<212> TYPE: PRT
<213> ORGANISM: Oryza sativa

<400> SEQUENCE: 23

Met Leu Pro Leu Arg Gly Cys His Arg Arg Leu Leu Ser Leu Arg Gly
1               5                   10                  15

Val Thr Ala Pro Ser Leu Leu Pro Pro Ile Thr Thr Thr Pro Thr Thr
            20                  25                  30

Ser Met Ala Ala Pro Gln Ser His Ser His Pro Ala Lys Thr Leu Arg
        35                  40                  45

Ala Ser Pro Pro Pro Ser Thr Ala Gly Ser Ala Pro Lys Arg Ser
    50                  55                  60

Arg Thr Met Ala Thr Asp Ala Ala Thr Ala His Ser Ala Ser Ala
65              70                  75                  80

Gly Cys Ser Ala Met Lys Ala Glu Phe Ala Lys His Ala Glu Tyr Leu
                85                  90                  95

Asn Thr Leu Asn Asp Lys Arg Glu Arg Leu Val Lys Ala Ser Arg Asp
            100                 105                 110

Leu Thr Met Asn Ser Lys Lys Ala Ile Phe Gln Val His Arg Ile Ser
        115                 120                 125

Lys Asn Asn Lys Glu Glu Val Leu Ser Lys Ala Glu Asn Asp Leu Thr
130                 135                 140

Val Val Val Asn Gln Tyr Ile Gly Lys Leu Val Lys Glu Leu Gln Gly
145                 150                 155                 160

Thr Asp Phe Trp Lys Leu Arg Arg Ala Tyr Thr Phe Gly Val Gln Glu
                165                 170                 175

Tyr Val Glu Ala Ala Thr Phe Cys Arg Phe Cys Lys Thr Gly Thr Leu
            180                 185                 190

Leu Ser Leu Ala Glu Ile Asn Asp Ser Leu Leu Glu Leu Gly Asp Lys
        195                 200                 205

Ser Val Glu Pro Leu Gln Ile Asn Val Leu Asp Tyr Val Leu Gly Val
210                 215                 220

Ala Asp Leu Ser Gly Glu Leu Met Arg Leu Ala Ile Gly Arg Ile Ser
225                 230                 235                 240

Asp Gly Glu Val Glu Tyr Ala Lys Asn Ile Cys Ala Phe Val Arg Asp
                245                 250                 255

Ile Tyr Arg Glu Leu Thr Leu Val Pro Leu Met Asp Asp Asn Ser
            260                 265                 270

Glu Met Lys Lys Lys Met Glu Thr Met Leu Gln Ser Val Val Lys Ile
        275                 280                 285

Glu Asn Ala Cys Phe Ser Val His Val Arg Gly Ser
    290                 295
```

```
                        290                 295                 300
```

<210> SEQ ID NO 24
<211> LENGTH: 93
<212> TYPE: PRT
<213> ORGANISM: Lycopersicon esculentum

<400> SEQUENCE: 24

```
Ile Arg His Glu Leu Ala Ala Thr Tyr Asp Ala Ile Gly Arg Val Asp
 1               5                  10                  15

Asp Ala Ile Glu Ile Leu Glu Tyr Val Leu Lys Leu Arg Glu Glu Lys
            20                  25                  30

Leu Gly Thr Ala Asn Pro Asp Phe Asn Asp Glu Lys Lys Arg Leu Ala
        35                  40                  45

Glu Leu Leu Lys Glu Ala Gly Arg Ser Arg Asn Lys Asn Pro Asn Ser
    50                  55                  60

Leu Glu Asn Leu Ile Asp Pro Asn Ser Lys Arg Thr Thr Lys Lys Glu
65                  70                  75                  80

Thr Ser Ser Lys Lys Trp Ser Ala Phe Gly Phe Arg Ser
                85                  90
```

<210> SEQ ID NO 25
<211> LENGTH: 248
<212> TYPE: PRT
<213> ORGANISM: Arabidopsis thaliana

<400> SEQUENCE: 25

```
Thr Gly Lys Leu Arg Glu Ser Lys Ser Tyr Cys Glu Asn Ala Leu Arg
 1               5                  10                  15

Ile Tyr Asn Lys Pro Val Pro Gly Thr Thr Val Glu Glu Ile Ala Gly
            20                  25                  30

Gly Leu Thr Glu Ile Ser Ala Ile Tyr Glu Ser Val Asp Glu Pro Glu
        35                  40                  45

Glu Ala Leu Lys Leu Leu Gln Lys Ser Met Lys Leu Leu Glu Asp Lys
    50                  55                  60

Pro Gly Gln Gln Ser Ala Ile Ala Gly Leu Glu Ala Arg Met Gly Val
65                  70                  75                  80

Met Tyr Tyr Thr Val Gly Arg Tyr Glu Asp Ala Arg Asn Ala Phe Glu
                85                  90                  95

Ser Ala Val Thr Lys Leu Arg Ala Ala Gly Glu Lys Ser Ala Phe Phe
            100                 105                 110

Gly Val Val Leu Asn Gln Met Gly Leu Ala Cys Val Gln Leu Phe Lys
        115                 120                 125

Ile Asp Glu Ala Gly Glu Leu Phe Glu Glu Ala Arg Gly Ile Leu Glu
    130                 135                 140

Gln Glu Arg Gly Pro Cys Asp Gln Asp Thr Leu Gly Val Tyr Ser Asn
145                 150                 155                 160

Leu Ala Ala Thr Tyr Asp Ala Met Gly Arg Ile Glu Asp Ala Ile Glu
                165                 170                 175

Ile Leu Glu Gln Val Leu Lys Leu Arg Glu Glu Lys Leu Gly Thr Ala
            180                 185                 190

Asn Pro Asp Phe Glu Asp Glu Lys Lys Arg Leu Ala Glu Leu Leu Lys
        195                 200                 205

Glu Ala Gly Arg Ser Arg Asn Tyr Lys Ala Lys Ser Leu Gln Asn Leu
    210                 215                 220

Ile Asp Pro Asn Ala Arg Pro Pro Lys Lys Glu Ser Ser Ala Lys Lys
```

```
                225                 230                 235                 240

Trp Pro Ser Leu Gly Phe Lys Phe
                        245

<210> SEQ ID NO 26
<211> LENGTH: 220
<212> TYPE: PRT
<213> ORGANISM: Arabidopsis thaliana

<400> SEQUENCE: 26

Thr Gly Lys Val Arg Glu Ala Lys Ser Tyr Cys Glu Asn Ala Leu Arg
        1               5                   10                  15

Ile Tyr Glu Ser His Asn Leu Glu Ile Ser Pro Glu Ile Ala Ser
                    20                  25                  30

Gly Leu Thr Asp Ile Ser Val Ile Cys Glu Ser Met Asn Glu Val Glu
                35                  40                  45

Gln Ala Ile Thr Leu Leu Gln Lys Ala Leu Lys Ile Tyr Ala Asp Ser
            50                  55                  60

Pro Gly Gln Lys Ile Met Ile Ala Gly Ile Glu Ala Gln Met Gly Val
        65                  70                  75                  80

Leu Tyr Tyr Met Met Gly Lys Tyr Met Glu Ser Tyr Asn Thr Phe Lys
                        85                  90                  95

Ser Ala Ile Ser Lys Leu Arg Ala Thr Gly Lys Lys Gln Ser Thr Phe
                    100                 105                 110

Phe Gly Ile Ala Leu Asn Gln Met Gly Leu Ala Cys Ile Gln Leu Asp
                115                 120                 125

Ala Ile Glu Glu Ala Val Glu Leu Phe Glu Glu Ala Lys Cys Ile Leu
            130                 135                 140

Glu Gln Glu Cys Gly Pro Tyr His Pro Glu Thr Leu Gly Leu Tyr Ser
        145                 150                 155                 160

Asn Leu Ala Gly Ala Tyr Asp Ala Ile Gly Arg Leu Asp Asp Ala Ile
                        165                 170                 175

Lys Leu Leu Gly His Val Val Gly Val Arg Glu Glu Lys Leu Gly Thr
                    180                 185                 190

Ala Asn Pro Val Thr Glu Asp Glu Lys Arg Arg Leu Ala Gln Leu Leu
                195                 200                 205

Lys Glu Ala Gly Asn Val Thr Gly Arg Lys Ala Lys
            210                 215                 220

<210> SEQ ID NO 27
<211> LENGTH: 482
<212> TYPE: PRT
<213> ORGANISM: Lycopersicon esculentum

<400> SEQUENCE: 27

Met Glu Ala Glu Asn Ser Asn Ala Ser Arg Ala Glu Glu Leu Lys Gln
        1               5                   10                  15

Leu Ala Asn Glu Ala Phe Lys Gly His Lys Tyr Ser Gln Ala Ile Asp
                    20                  25                  30

Leu Tyr Thr Gln Ala Ile Glu Leu Asn Gly Glu Asn Ala Val Tyr Tyr
                35                  40                  45

Ala Asn Arg Ala Phe Ala His Thr Lys Leu Glu Glu Tyr Gly Ser Ala
            50                  55                  60

Ile Gln Asp Gly Thr Arg Ala Ile Glu Ile Asp Pro Arg Tyr Ser Lys
        65                  70                  75                  80

Gly Tyr Tyr Arg Arg Gly Ala Ala Tyr Leu Ala Met Gly Lys Phe Lys
```

```
                    85                  90                  95
Asp Ala Leu Lys Asp Phe Gln Gln Val Lys Lys Leu Cys Pro Asn Asp
            100                 105                 110
Pro Asp Ala Thr Lys Lys Leu Lys Glu Cys Glu Lys Ala Val Met Lys
            115                 120                 125
Leu Lys Phe Glu Glu Ala Ile Ser Val Pro Glu Ser Gln Arg Arg Ser
            130                 135                 140
Val Ala Asp Ser Ile Asp Tyr Arg Ser Val Glu Val Glu Pro Gln Tyr
145                 150                 155                 160
Ala Gly Ala Arg Ile Glu Gly Asp Val Val Thr Leu Asp Phe Val Lys
            165                 170                 175
Lys Met Leu Asp Asp Phe Lys Asn Gln Lys Asn Leu His Lys Arg Tyr
            180                 185                 190
Ala Tyr Gln Ile Val Leu Gln Thr Arg Glu Met Leu Arg Ala Leu Pro
            195                 200                 205
Ser Leu Val Asp Ile Val Val Pro Glu Gly Lys His Phe Thr Val Cys
            210                 215                 220
Gly Asp Val His Gly Gln Phe Tyr Asp Leu Leu Asn Ile Phe Glu Leu
225                 230                 235                 240
Asn Gly Leu Pro Ser Glu Asp Asn Pro Tyr Leu Phe Asn Gly Asp Phe
            245                 250                 255
Val Asp Arg Gly Ser Phe Ser Leu Glu Val Ile Leu Thr Leu Phe Ala
            260                 265                 270
Phe Lys Cys Met Cys Pro Ser Ala Ile His Leu Ala Arg Gly Asn His
            275                 280                 285
Glu Ser Lys Ser Met Asn Lys Ile Tyr Gly Phe Glu Gly Glu Val Arg
290                 295                 300
Ser Lys Leu Ser Glu Ile Phe Val Glu Leu Phe Ala Glu Val Phe Cys
305                 310                 315                 320
Cys Leu Pro Leu Ala His Val Ile Asn Glu Lys Val Phe Val Val His
            325                 330                 335
Arg Gly Leu Phe Ser Val Asp Gly Val Lys Leu Ser Asp Ile Arg Ala
            340                 345                 350
Ile Asp Arg Phe Cys Glu Pro Glu Glu Gly Leu Met Cys Glu Leu
            355                 360                 365
Leu Trp Ser Asp Pro Gln Pro Gln Pro Gly Arg Gly Pro Ser Lys Arg
            370                 375                 380
Gly Val Gly Leu Ser Phe Gly Gly Asp Val Thr Lys Arg Phe Leu Gln
385                 390                 395                 400
Glu Asn Asn Leu Asp Leu Val Val Arg Ser His Glu Val Lys Asp Glu
            405                 410                 415
Gly Tyr Glu Ile Glu His Asp Gly Lys Leu Ile Thr Val Phe Ser Ala
            420                 425                 430
Pro Asn Tyr Cys Asp Gln Met Gly Asn Lys Gly Ala Phe Ile Arg Phe
            435                 440                 445
Glu Ala Pro Asp Met Lys Pro Asn Ile Val Thr Phe Ser Ala Val Pro
            450                 455                 460
His Pro Asp Val Lys Pro Met Ala Tyr Ala Asn Asn Phe Leu Arg Met
465                 470                 475                 480
Phe Ser

<210> SEQ ID NO 28
<211> LENGTH: 533
```

```
<212> TYPE: PRT
<213> ORGANISM: Arabidopsis thaliana

<400> SEQUENCE: 28

Met Glu Thr Lys Asn Glu Asn Ser Asp Val Ser Arg Ala Glu Phe
 1               5                  10                  15

Lys Ser Gln Ala Asn Glu Ala Phe Lys Gly His Lys Tyr Ser Ser Ala
                20                  25                  30

Ile Asp Leu Tyr Thr Lys Ala Ile Glu Leu Asn Ser Asn Asn Ala Val
            35                  40                  45

Tyr Trp Ala Asn Arg Ala Phe Ala His Thr Lys Leu Glu Glu Tyr Gly
        50                  55                  60

Ser Ala Ile Gln Asp Ala Ser Lys Ala Ile Glu Val Asp Ser Arg Tyr
65                  70                  75                  80

Ser Lys Gly Tyr Tyr Arg Arg Gly Ala Ala Tyr Leu Ala Met Gly Lys
                85                  90                  95

Phe Lys Asp Ala Leu Lys Asp Phe Gln Gln Val Lys Arg Leu Ser Pro
            100                 105                 110

Asn Asp Pro Asp Ala Thr Arg Lys Leu Lys Glu Cys Glu Lys Ala Val
        115                 120                 125

Met Lys Leu Lys Phe Glu Glu Ala Ile Ser Val Pro Val Ser Glu Arg
130                 135                 140

Arg Ser Val Ala Glu Ser Ile Asp Phe His Thr Ile Gly Asn Lys Pro
145                 150                 155                 160

Arg Ser Ser Ser Met Pro Thr Lys Thr Ala Leu Ala Ala Val Val Ala
                165                 170                 175

Ala Val Met Val Val Ala Val Arg Gly Phe Ala Thr Thr Glu Ile Leu
            180                 185                 190

Met Val Leu Val Ser Val Val Leu Gly Thr Phe Trp Trp Glu Val Glu
        195                 200                 205

Pro Gln Tyr Ser Gly Ala Arg Ile Glu Gly Glu Val Thr Leu Asp
    210                 215                 220

Phe Val Lys Thr Met Met Glu Asp Phe Lys Asn Gln Lys Thr Leu His
225                 230                 235                 240

Lys Arg Tyr Ala Tyr Gln Ile Val Leu Gln Thr Arg Gln Ile Leu Leu
                245                 250                 255

Ala Leu Pro Ser Leu Val Asp Ile Ser Val Pro His Gly Lys His Ile
            260                 265                 270

Thr Val Cys Gly Asp Val His Gly Gln Phe Tyr Asp Leu Leu Asn Ile
        275                 280                 285

Phe Glu Leu Asn Gly Leu Pro Ser Glu Asn Pro Tyr Leu Phe Asn
    290                 295                 300

Gly Asp Phe Val Asp Arg Gly Ser Phe Ser Val Glu Ile Ile Leu Thr
305                 310                 315                 320

Leu Phe Ala Phe Lys Cys Met Cys Pro Ser Ile Tyr Leu Ala Arg
                325                 330                 335

Gly Asn His Glu Ser Lys Ser Met Asn Lys Ile Tyr Gly Phe Glu Gly
            340                 345                 350

Glu Val Arg Ser Lys Leu Ser Glu Lys Phe Val Asp Leu Phe Ala Glu
        355                 360                 365

Val Phe Cys Tyr Leu Pro Leu Ala His Val Ile Asn Gly Lys Val Phe
    370                 375                 380

Val Val His Gly Gly Leu Phe Ser Val Asp Gly Val Lys Leu Ser Asp
385                 390                 395                 400
```

```
Ile Arg Ala Ile Asp Arg Phe Cys Glu Pro Pro Glu Glu Gly Leu Met
                405             410                 415

Cys Glu Leu Leu Trp Ser Asp Pro Gln Pro Leu Pro Gly Arg Gly Pro
            420             425             430

Ser Lys Arg Gly Val Gly Leu Ser Phe Gly Gly Asp Val Thr Lys Arg
        435             440             445

Phe Leu Gln Asp Asn Asn Leu Asp Leu Leu Val Arg Ser His Glu Val
    450             455             460

Lys Asp Glu Gly Tyr Glu Val Glu His Asp Gly Lys Leu Ile Thr Val
465         470             475             480

Phe Ser Ala Pro Asn Tyr Cys Asp Gln Met Gly Asn Lys Gly Ala Phe
            485             490             495

Ile Arg Phe Glu Ala Pro Asp Met Lys Pro Asn Ile Val Thr Phe Ser
            500             505             510

Ala Val Pro His Pro Asp Val Lys Pro Met Ala Tyr Ala Asn Asn Phe
        515             520             525

Leu Arg Met Phe Asn
    530
```

NUCLEOTIDE SEQUENCES CODING SIGNAL TRANSDUCTION COMPONENTS IN DURABLE AND BROAD-RANGE RESISTANCE STRATEGIES BASED ON PLANT DEFENCE

This application is a Continuation of copending PCT International Application No. PCT/EP01/06458 filed on May 18, 2001, which was published in English and which designated the United States and on which priority is claimed under 35 U.S.C. § 120, the entire contents of which are hereby incorporated by reference.

The invention pertains to nucleotide sequences coding for polypeptides that are capable of functioning as signal transduction components. These nucleotides preferably, but not necessarily, are capable of interfering with the defence system and specifically the resistance of plant crops to various pathogens.

The present invention further relates to the products, especially polypeptide products that are encoded by said nucleotide sequences. The present invention further relates to the use of said nucleotide sequences and products encoded by said nucleotide sequences in inducing, activating, contributing, enhancing, (down)regulating or otherwise exerting an influence on the defence mechanism and in particular the resistance of plants against pathogens and more in particular to soil plant pathogens.

Disease management in agriculture largely depends on the breeding of cultivars that carry monogenic resistances against a variety of pathogens. Often these resistances are absolute and specific for one race or for one pathogen only. This puts a selective pressure on the pathogen that results in the evolution of the pathogen and, usually, in the appearance of new races and/or varieties of the pathogens which break the resistance. Breeding for broader tolerance against pathogen infections (horizontal resistance) would circumvent this selective pressure. However, in practice this is often experienced as cumbersome, for such traits are generally determined by multiple loci.

Using molecular techniques various natural disease resistance genes have been isolated during the last five years. However, their use in molecular breeding programs is limited since they code for resistance to one race or variety of a pathogen only. To engineer broad spectrum resistance traits very different strategies are being pursued. The most widespread approach for instance used for fungus resistance is the expression of genes encoding proteins inhibiting fungal growth. In the last few years strategies for fungal resistance have been explored based on the induction by pathogens of cell death at the site of infection.

Plant pathogen interactions result either in an invasion of the plant by the pathogen, causing disease symptoms and eventually the death of the plant, or in an infection localized in a restricted area of plant tissue or even in a few cells. Localization of infection is due to defence reactions of the plant. The defence response best studied thusfar is the race-specific resistance reaction brought about by single, dominant resistance (R-) genes. Genetically, race-specific resistance is, in theory, explained by the gene-for-gene hypothesis which states that the outcome of a plant pathogen interaction is determined by the simultaneous presence of both an avirulence (avr) gene in the pathogen and the corresponding R-gene in the host (Flor, 1971). Biochemically, the product of a pathogen avr-gene, i.e. the race specific elicitor, is thought to be recognized by a specific receptor, i.e. the product of a corresponding R-gene in the plant; upon recognition expression of resistance is induced.

For many interactions the existence of both an R-gene and a corresponding avr-gene has been proven, and so far more than 20 R-genes have been cloned. In a few cases corresponding pathogen avr-genes have been isolated as well. The primary structures of the products of the cloned R-genes seem to confirm the receptor-like character of these proteins (Staskawicz et al. 1995). In addition, the conserved structure of the proteins encoded by the R-genes suggests that the defence responses, induced upon recognition of a race-specific elicitor, are likely to contain conserved signal transduction components. So far, no conserved sequence information has been observed in avr-gene products despite their functional similarity.

It is a goal of the present invention to provide for durable resistance in crops. It is a further goal of the present invention to identify nucleotide sequences and/or polypeptides that are related to, or capable of controlling, inducing, contributing or otherwise exercise a negative or positive influence or stimulus to, the signal transduction pathway. Also a goal of the present invention is to provide for compounds or compositions that find use and/or application in the activation or regulation (up or down) of the defence mechanism of plants and in particular of the defence mechanism of plants against pathogens, more in particular against soil-pathogens. It is further a goal of the present invention to provide for downstream signaling components that are related to or are involved in the regulation of resistance, preferably race-specific resistance. Other goals of the present invention will become apparent from the description of the invention and its embodiments.

The present invention now provides for downstream signaling components of race-specific resistance. The invention further provides access to compositions, including nucleotide sequences and/or polypeptide products that can be used in the activation or (up) regulation of defence mechanisms in plants against pathogens, in particular against soil plant pathogens. The invention also provides components that can be used for the generation of broad resistance in plants against plant pathogens.

Race specific resistance is established by resistance (R-) gene products that recognize pathogen-race derived ligands. The recognition signal is transduced by the R-gene product into a defence response by activating downstream signaling molecules. Recent research suggest that different R-genes utilize identical downstream components (EDS-1, NDR-1 from Arabidopsis). R-gene independent activation of such genes might therefor trigger defence reactions independently of specific pathogen recognition.

The present inventors have now identified downstream signaling genes starting from particular resistance genes, i.e. the I-2 gene from tomato and/or the Mi gene from tomato and have identified proteins that physically interact with the resistance gene I-2 product from tomato and/or with the resistance gene Mi product from tomato.

The present inventors have further found that resistance against a broad spectrum of pathogens can be achieved by the present findings and, accordingly, the I-2 and Mi genes described herein merely function as starting point for the identification of a wider inventive concept being the application of compounds or molecules that are involved in the signal transduction pathway in the generation of broad spectrum resistance. The present invention hence encompasses also the identification of downstream signaling genes, which upon activation are capable of inducing or enhancing a defence response in a wide variety of plants against a wide variety of pathogens. Other findings of the present inventors will become apparent from the description and/or the examples.

The I-2 gene confers resistance to the soil borne pathogen *Fusarium oxysporum* f.sp. *lycopersici* (Fol), carrying avirulence gene 2 such as disclosed in WO97/06259 and incorporated herein by reference. The protein encoded by the I-2 gene contains a nucleotide binding site (NBS), a leucine zipper (LZ) domain and a leucine rich repeat region (LRR). These regions show homologies to similar domains in proteins encoded by other R-genes including RPM1, RPS2, L6 and many others.

The Mi gene confers broad resistance against nematodes and/or aphids. The Mi gene, such as disclosed in WO 98/06750 and incorporated herein by reference is the first identified R-gene that is capable of expressing a dual functionality, i.e. against nematodes and aphids. More in particular, the Mi is capable of conferring resistance to nematodes, more in particular root-knot nematodes, especially Meloidogyne spp. such as *M. incognita, M. arenaria, M. javanica* and to aphids, in particular potato aphids, preferably *Macrosiphum euphorbiae* and related species and in different plants.

In a first aspect the invention thus relates to a nucleotide sequence, preferably an isolated nucleotide sequence, derived from a plant genome encoding a polypeptide product which product can be activated as a signaling molecule in the signal transduction pathway of resistance to a plant pathogen wherein said resistance results from the interaction between polypeptide products encoded by a resistance gene and elicitors encoded by an avirulence gene in said plant pathogen.

According to a preferred embodiment of the invention, the plant pathogen is a soil plant pathogen. More in particular the pathogen is selected from fungi, especially *Fusarium oxysporum, Verticillium dahliae, Cladosporium,* and *Ralstona Solanaceum*, nematodes such as from the species *Meloidogyne, Heterodera, Globodera* and *Nacobbus*, aphids such as from the species *Macrosiphum*, viruses such as exemplified by Tomato spotted wilt virus (TSWV), bacteria such as exemplified by *Clavibacter* and other plant pathogens such as *Xanthomonas* and *Pseudomonas*

The expression "derived from a plant genome" indicates that the nucleotide sequence can be isolated from a plant genome, but the expression also encompasses any sequence whatever its preparation process or its origin, which can be prepared or obtained on basis of the knowledge of the nucleotide sequence and/or of the function of the original nucleotide sequence present in the plant genome. In other words, the nucleotide sequences of the invention are not necessarily obtained directly from the plant genome. In a preferred embodiment, they are derivable from said genome. Especially said sequence can be derived from material present in sequence libraries, or synthesized. Nucleotide sequences according to the invention therefore encompass any nucleotide sequence identical or modified (including fragments thereof) with respect to the original identified sequence from the plant, provided its structure and/or activity within the scope of the present invention is maintained, improved, repressed or modified with respect to the activity of the originally identified plant sequence for the purpose of the invention. The invention thus encompasses nucleotide sequences that are homologues and preferably functional homologues of the nucleotide sequences according to the invention.

The term "homologous" in terms of the present invention indicates a certain amount of sequence identity on the nucleotide level.

In order to compare the sequence which homology is examined, with the original sequence optimal alignment over at least a region of the sequences may be performed, when said region is identified as a conserved region. Such comparison may be achieved with the BLAST algorithm or a comparable method.

Comparison of sequences in order to determine whether they are homologous in accordance with the definition of the present invention, can also be carried out by computerized implementation of algorithms such as FASTA, TFASTA or BESTFIT. 100% homology indicates that the sequences are 100% identical. Sequences are also considered homologous if one or more nucleotides from the sequence are deleted, added or replaced as long as a certain percentage of sequence identity remains, for instance with a most preferred limit of 99%, more preferably 95, 85, 80, preferably 75, 70 or 65%. Also percentages as low as 50 or 60% may very well be considered as homologous. Whether or not a sequence can be regarded as homologous also depends on the function of that sequence. For instance a nucleotide sequence encoding a protein will still be considered as homologous if the protein it encodes is able to perform substantially the same function as the protein encoded by the original sequence. Hence homology is present if the functionality is maintained, thereby allowing for well-known principles as degeneracy.

By the term "functionally homologous" is meant the following. A sequence (for instance a gene) is considered functionally homologous if that sequence (gene) is homologous to another sequence, hence at least one nucleotide is deleted, inserted, replaced such as inversed (in case of more than one nucleotide) or transversion (purine-pyrimidine or pyrimidine-purine substitution) or transition (purine-purine or pyrimidine-pyrimidine substitution) while the function of said sequence (gene) is substantially maintained. This may also apply to chemically modified sequences. When a sequence is functionally homologous, there may very well be a low percentage of homology, but the functionality of that sequence is substantially maintained.

The nucleotide sequences according to the invention encompass DNA, RNA or cDNA are also included within the scope of the present invention.

A nucleotide sequence according to the invention can have essentially the same length as the original sequence from the plant or can be shorter or longer.

A nucleotide sequence according to the invention encompasses sequences which are shorter than the original sequence from the plant genome. Such shorter sequences may be designated as "fragments" in the following pages. The expression "nucleotide sequence" however generally encompasses fragments as defined hereafter.

A fragment in terms of the present invention is regarded as a 'functional fragment' if the function of that fragment compared to the original sequence from the plant genome is substantially maintained. This may also apply to chemically modified fragments. When a fragment is a functional fragment, there may very well be a low percentage of homology to the original sequence from the plant genome, but the functionality of that fragment is substantially maintained. Such sequences, whether DNA, cDNA or RNA are also included within the scope of the present invention.

The length of the fragments may vary from about 50 nucleotides (nt) up to a length equaling the length (in nucleotides) of the original nucleotide sequence derived from the plant genome. Preferably the total length of the nucleotide sequence is at least 10 nt, preferably 15 nt, particularly at least about 50 nt, more particularly at least about 100 nt, especially at least about 150 nt, more especially at least about 200 nt, quite especially at least about 500 nt or at least about 1000 nt. It is expected that there is no upper limit to the total length of the nucleotide sequence, other than the total length of the original nucleotide sequence derived from the plant genome.

A nucleotide sequence according to the invention is preferably capable of hybridizing to the coding part of the original sequence present in the plant genome. Appropriate conditions for the determination of substantially identical nucleotide sequences is if two molecules hybridize to each other under these conditions. Appropriate conditions can vary from low to high stringency and will be different under different circumstances. Generally, stringent conditions are selected to be about 5° C. to about 20° C. lower than the thermal melting point Tm for a specific sequence at a defined ionic strength and pH. The Tm is the temperature (under a defined ionic strength and pH) at which 50% of the target sequence hybridizes to a perfectly matched probe. Typically, stringent wash conditions are those in which the salt concentration is about 0,02 molar at pH 7 and the temperature is at least about 50° C.

Stringent conditions refer to hybridisation conditions which allow a nucleic acid sequence to hybridise to a particular sequence. In general, high stringent conditions refer to the hybridisation conditions which allow a nucleic acid sequence of at least 50 nucleotides and preferably about 200 or more nucleotides to hybridise to a particular sequence at about 65° C. in a solution comprising about 1 M salt, preferably 6×SSC or any other solution having a comparable ionic strength, and washing at 65° C. in a solution comprising about 0, 1 M salt, or less, preferably 0, 2×SSC or any other solution having a comparable ionic strength. These conditions allow the detection of sequences having about 90% or more sequence identity. In general, lower stringent conditions refer to the hybridisation conditions which allow a nucleic acid sequence of at least 50 nucleotides and preferably about 200 or more nucleotides to hybridise to a particular sequence at about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. These conditions allow the detection of sequences having up to 50% sequence identity. The person skilled in the art will be able to modify these hybridisation conditions in order to identify sequences varying in identity between 50% and 90%.

A nucleotide sequence according to the invention can be any type of nucleotide sequence including DNA, RNA and especially can be genomic or synthetic DNA sequence for instance a complementary DNA sequence (cDNA). A sequence according to the invention can be used in a sense or in an antisense orientation for the purpose of the invention, preferably in an antisense orientation.

A nucleotide sequence according to the invention is in general capable of encoding a polypeptide product. This encompasses nucleotide sequences corresponding to the Open Reading Frame (ORF) capable of being expressed as an amino acid sequence. It also encompasses the nucleotide sequence provided with the necessary or appropriate control elements such as exemplified by a promoter or enhancers and other well known sequences. These sequences for control especially include promoter sequences. Such control elements are in general operably linked to said nucleotide sequence.

In terms of the present invention the term 'operably linked' includes reference to a functional linkage between the control element and the nucleotide sequence according to the invention. In the case of a promoter operably linked to the nucleotide according to the invention, the promoter initiates and mediates transcription of the nucleotide sequence according to the invention. Generally, operably linked means that the nucleic acid sequences of the promoter and the nucleotide sequence according to the invention being linked are contiguous and, where necessary to join two coding regions, contiguous and in the same reading frame.

The control of the transcription and/or expression may be directed by homologous sequences or heterologous with respect to the coding sequences.

The nucleotide sequence according to the present invention comprises and preferably corresponds to the nucleotide sequence of the Open Reading Frame. This sequence is capable of encoding the amino acid sequence of the polypeptide product. This polypeptide product can be activated in plant or a plant part as a signaling element, especially a signaling molecule in the signal transduction pathway of resistance of said plant to plant pathogens, especially soil plant pathogens, as a result of the interaction between polypeptide products encoded by resistance genes and race specific elicitors encoded by avirulence genes in said plant pathogens.

According to one embodiment, the nucleotide sequence of the invention is a fragment of the sequence of the ORF. According to one further embodiment, this sequence fragment encodes for a polypeptide that is a part of the signaling molecule encoded by the entire ORF, provided that the essential activity of the original signaling molecule related to the purpose of the invention is substantially maintained.

According to the above definitions, the putative function or activity of the polypeptide product encoded by the nucleotide sequence of the invention is disclosed with respect to the function which has been observed for said sequence in the resistance mechanism to plant pathogens, especially in the signal transduction pathway when it is expressed in an biological environment that permits the expression of its activity.

In another aspect the invention is also directed to a nucleotide sequence defined according to one or several definitions herein disclosed, including any available combination of embodiments, in a process or a use that would confer to said sequences a different function or that would enable said sequence, or any sequence capable of hybridizing to said sequence, to be active in a different biological environment from its natural one. This applies for instance when the nucleotide sequences or the encoded products therefrom are used in a non race-specific defence mechanism against pathogens, in particular plant pathogens. This applies for instance when the nucleotide sequences or the encoded products therefrom are used in a non race-specific defence mechanism against pathogens, preferably in different plant species or crops.

In one embodiment of the invention, the nucleotide sequence according to the invention encodes for a polypeptide product that is capable of interacting with the N-terminal part or with the C-terminal part of the polypeptide product encoded by the resistance gene to plant pathogens, especially soil plant pathogens. In this embodiment the resistance gene is preferably I-2, but the Mi gene is capable of similar interactions. One of the differences between the Mi gene and the I-2 gene resides in the N-terminal part of the respective polypeptides encoded by the two genes. Based thereon these genes are generally classified in different classes of R-genes. The present invention demonstrates that by the sequences and products of the present invention that interference with the signal transduction pathway provides for a method of conferring resistance that is substantially independent of the pathogen or the resistance gene or the theoretical classification of the resistance gene. The examples will provide further evidence that the present invention also incorporates the generation of resistance against various pests or pathogens and preferably in various plants.

By the expression "N-terminal part of the polypeptide product" is understood that the sequences concerned are those of the first ⅔ of the sequence of the polypeptide. By the expression "C-terminal part of the polypeptide product" is understood that the sequences concerned are those of the last ⅓ of the sequence of the polypeptide.

In one preferred embodiment the invention relates to a nucleotide sequence derived from a plant genome that encodes a polypeptide product that is capable of interacting with the polypeptide product encoded by the I-2 resistance gene and/or the Mi resistance gene.

In one especially preferred embodiment the invention relates to a nucleotide sequence derived from a plant genome that encodes a polypeptide product that is capable of interacting with the polypeptide product encoded by the I-2 resistance gene.

The I-2 resistance gene has been disclosed in European patent application 843727 and in WO97/06259.

The inventors have observed that as a result of experiments performed by using the I-2 and/or the Mi gene that two groups of nucleotide sequences of the invention, also designated as interactor sequences, have been identified with respect to their interaction, especially physical interaction, with the I-2 polypeptide product and/or the Mi-polypeptide product.

Accordingly, in one aspect, the invention pertains to nucleotide sequences that interact with the N-terminal part of the polypeptide product encoded by the I-2 resistance gene and on the other hand to nucleotide sequences encoding for polypeptide products that interact with the C-terminal part of the polypeptide product encoded by the I-2 resistance gene.

The invention also pertains to nucleotide sequences that interact with at least part of the polypeptide product encoded by the Mi resistance gene.

The invention further pertains to nucleotide sequences that interact with at least a part or a fragment of the polypeptide product encoded by the Mi resistance gene and/or the I-2 resistance gene.

The terms 'Mi resistance gene' and 'I-2 resistance gene' will encompass, as will be recognized by those skilled in the art, sequences that need not be exactly identical to the sequence of the Mi and I-2 gene such as disclosed in W098/06750 and WO 97/06259, respectively but also encompass nucleotide sequences that are substantially identical.

Two polynucleotides or polypeptides are said to be 'identical' if the sequence of nucleotides or amino acid residues, respectively, in the two sequences is the same when aligned for maximum correspondence. The term 'complementary to' is used herein to mean that the complementary sequence is capable of base pairing to all or a specified contiguous portion of a reference polynucleotide sequence. The term 'substantially identical' for polynucleotide or polypeptide sequences means that a polynucleotide or polypeptide sequence has at least 55% or 60% sequence identity relative to the reference polynucleotide sequence, generally at least 65%, preferably at least 70% or 75% more preferably at least 80% and most preferably at least 90%. The skilled artisan will recognize that these percentages can be appropriately adjusted by taking into account codon degeneracy, amino acid similarity, reading frame positioning, conservative amino acid substitutions and the like. These definitions also apply, where appropriate, to the descriptions of homology and functional homology of sequences.

A particular preferred embodiment of the present invention is a nucleotide sequence that encodes for a signal transduction component.

One of the ways in which the interaction between the products encoded by the nucleotide sequences according to the invention and the products encoded by the nucleotide sequences related to the resistance genes I-2 and/or Mi, is determined is according to the assays described in the following experimented procedures.

One method which is suitable for the identification of the nucleotides according to the invention is based on the yeast two-hybrid technology, described in the prior art. This method enables the detection of protein-protein interaction. Two-hybrid systems are commercially available for instance from the company CLONTECH (Palo-Alto, Calif. USA).

The two-hybrid system is a method for the determination of protein-protein interactions wherein a bait component is constructed that comprises a vector comprising a nucleotide sequence of, in this case, a resistance gene of a determined plant directing the expression of the polypeptide product, fused to a DNA-binding moiety. A prey component is prepared that comprises a sequence or a sequence library to be assayed (preferably capable of encoding interactor proteins) which can be prepared from DNA, for instance cDNA, of a plant susceptible to a determined plant pathogen corresponding to said resistance gene of the bait component and recombined with an activation domain that functionally interacts with said binding domain. A third component is provided that comprises one or several reporter genes whose expression is made dependent from the interaction of the bait and prey components involving the interaction of the nucleotide of the resistance gene and the assayed nucleotide sequence.

In one embodiment of the present invention, the resistance gene of interest is the I-2 gene of tomato or a (functional) homologue or fragment thereof, especially a functional domain of said gene.

In one embodiment of the present invention, the resistance gene of interest is the Mi gene of tomato or a (functional) homologue or fragment thereof, especially a functional domain of said gene.

In one embodiment of the present invention, the resistance genes of interest are the I-2 gene and the Mi-gene of tomato or a (functional) homologue or fragment thereof, especially a functional domain of said genes, more preferably a functional domain that is common to both genes.

In one particular preferred embodiment, the bait component is constructed from a nucleotide sequence that has a feature that is commonly found in resistance genes, preferably in mono-genic resistance genes. Examples thereof are nucleotide sequences that, when properly expressed, encode for polypeptides having regions that are common to such R-genes. Examples of such regions are NBS domains, LRR motifs or LZ-motifs.

In the case of the Mi-gene, both LRR and LRR/NBS domains have been used as bait to identify the Mi-interactions of the present invention. Alternatively, the entire ORF of the Mi-gene can be used as bait.

The nucleotide sequence used in the construction of the bait component is recombined with the binding domain of a transcription factor and expressed in a determined yeast strain suitable to carry out the selection of the interactor proteins. This constitutes a bait component.

A prey component or a prey library is prepared wherein an appropriate vector is used to clone and express nucleotides sequences capable of encoding for polypeptide products that are interactor candidates to interact with the resistance gene of interest or (functional) homologue or fragment thereof. The resistance gene for which interactor candidates are identified are preferably the I-2 gene and/or the Mi gene.

The vector construct of the prey component is prepared such that the nucleotide sequences of the library are fused with an activation domain of the transcription factor capable of interacting with the binding domain as defined hereinbefore.

The vector is used to express the cloned library in the yeast strain expressing the bait. A screening of interactor proteins is performed to detect yeast transformants expressing marker genes whose expression is under the control of a promoter activated by the interaction between the binding domain of the bait and the activation domain of the prey through the interaction of the candidate interactor gene product and the polypeptide domain encoded by the nucleotide sequence of the resistance gene of the plant.

The invention in another aspect pertains to nucleotide sequences that are obtainable by a process comprising the steps of:
a) cloning into a yeast strain, one or several vectors comprising a construct comprising at least one determined region of a resistance gene to a plant pathogen, capable of encoding a polypeptide product of said resistance gene to a plant pathogen wherein said at least determined region of said resistance gene is fused to a sequence coding for a binding domain of a transcription factor capable of activating a reporter gene present in the vector and placed under the control of regulation sequences whose activation is dependent upon interaction of the binding domain and of the activation domain of the transcription factor,
b) cloning into on or several vectors, a nucleotide sequence of a cDNA library obtained from a plant which may be susceptible to said plant pathogen or is naturally resistant to said plant pathogen or has been rendered resistant to said plant pathogen, the cloned nucleotide sequences being fused in the vector, with a nucleotide sequence encoding the activation domain of said transcription vector,
c) expressing said vectors of steps a) and b) in said yeast strain,
d) identifying positive clones resulting in the activation of the marker gene cloned into the first or second vectors.

The plant pathogen is preferably a soil plant pathogen.

The invention also relates to a process for obtaining a nucleotide sequence as defined above, which process comprises or contains the above steps.

In one embodiment, the nucleotide sequence, preferably a cDNA fragment expressed by the positive clones of yeast, is identified and if appropriate isolated and optionally sequenced according to well known techniques.

In one embodiment, the present invention pertains to interactor sequences capable of interacting with the N-terminal domain of the I-2 polypeptide product. In one preferred embodiment, the inventions pertains to interactor sequences designated by interactor K-10, interactor K-23 and/or interactor K-6, represented in FIGS. 1–3, respectively. These sequences are presented as SEQ ID No 2, 4 and 6 respectively, in the Sequence Listing.

In another embodiment, the present invention pertains to interactor sequences capable of interacting with the C-terminal domain of the I-2 polypeptide product. In one preferred embodiment, the inventions pertains to interactor sequences designated by interactor J-49, interactor S-25, represented in FIGS. 4 and 5, respectively. These sequences are presented as the SEQ ID No 7 and 9 respectively, in the Sequence Listing.

In one embodiment, the present invention pertains to interactor sequences that are capable of interacting with the Mi-polypeptide product. In one preferred embodiment the interactor sequences are capable of interacting with both the I-2 and Mi polypeptide products.

In one aspect the present invention pertains to interactor sequences that are capable of hybridizing to the sequences depicted in FIGS. 1–5, preferably under stringent conditions as hereinbefore defined.

In one embodiment the present invention further pertains to interactor nucleotide sequences that are mutated and/or modified when compared to the original sequence derived from the genome in order to alter their activity in the defence reaction against pathogens in general and plant pathogens in particular. In one other embodiment the present invention further pertains to interactor nucleotide sequences that are mutated and/or modified in order to alter their specificity in the defence reaction against pathogens in general and plant pathogens in particular.

The invention is further directed to fragments of the presently disclosed nucleotide sequences and to fragments of the presently disclosed polypeptide sequences, provided they present the functional properties of the original sequences of interest within the scope of the present invention.

Preferably, said polypeptide fragments have a binding function involved in the interaction with polypeptide products produced by plants in the signal transduction pathway of resistance to pathogens.

Preferably said polypeptide fragments may vary from about 20 amino acids (aa) up to a length equaling the length (in amino acids) of the original polypeptide sequence encoded by the nucleotide sequence derived from the plant genome. Preferably the total length of the fragment polypeptide sequence is at least 10 aa, preferably 15 aa, particularly at least about 50 aa, more particularly at least about 100 aa, especially at least about 150 aa, more especially at least about 200 aa, quite especially at least about 500 aa or at least about 1000 aa. It is expected that there is no upper limit to the total length of the sequence, other than the total length of the original polypeptide sequence derived from the plant genome. The length of the fragments may of course be longer without departing from the gist of the invention.

Preferably, the nucleotide sequences and fragments according to the invention are capable of hybridizing with at least part of the active sequence of the original sequence derived from the plant genome.

The invention further relates to nucleotide sequences including fragments as defined above or polypeptides or fragments of polypeptides identified in a nucleotide sequence of the invention or encoded for by a nucleotide sequence of the invention in a determined plant which nucleotide/polypeptide sequences/fragments have similarities with nucleotide/polypeptide sequences/fragments from other plants. Preferably these similarities encompass shared, common or conserved regions or fragments of nucleotide strands or polypeptide strands.

Furthermore the invention encompasses nucleotide sequences or polypeptide sequences according to the invention that are specific for a determined plant species or different with respect to other plant species when compared to sequences having similarities in other plant species.

Related and/or specific domains in the compared sequences are identified by using antibody technology, especially monoclonal antibody technology directed against a determined domain, preferably a functional domain of the sequence of interest. Detecting the presence or absence of cross-reactions between the polypeptide product of the various sequences provides the desired identification.

According to one embodiment of the invention, the activity or specificity of the nucleotide sequence in the defence reaction against pathogens can be altered either to improve activity and specificity or to the contrary to lower said activity or specificity. Such alterations are very advantageously in the case that a broad spectrum of resistance in plants is required.

The invention further relates to recombinant nucleotide sequences which comprises a nucleotide sequence according to one or more of the above definitions and wherein the nucleotide sequence is placed under the control of a pathogen induced promoter. The recombinant nucleotide sequence according to the invention is in particular a sequence wherein the promoter is a foliar or root pathogen indcued promoter. Examples of such pathogen induced promoters which can be used in an embodiment of the invention are CAMV35S promoter, the potato GST promoter, the I-2 promoter.

The invention further pertains to a recombinant vector comprising a nucleotide sequence according to one or several of the above definitions. The nucleotide sequence can be cloned into the vector in a sense or an antisense orientation. It is preferred that the nucleotide sequence is cloned into the vector in an antisense orientation. The effect of cloning said sequence in an antisense orientation is also advantageously achieved by the use of other interfering RNAs in general such as exemplified by amplicons, inverted repeat structures or dsRNA and other techniques that lead to PTGS (Post Transcriptional Gene Silencing).

By using the sequences according to the invention in an sense orientation, the overexpression of genes can be achieved. This can also lead to the induction of the desired resistance against a pathogen.

The invention further relates to cells transformed with a nucleotide sequence or a recombinant sequence or a vector according to the invention, especially cells which are selected from the group consisting of bacteria, yeasts and plant cells.

The invention is also directed to plants transformed with a nucleotide sequence as hereinbefore defined or with a recombinant sequence or a vector according to one or several of the above definitions.

Plants can be selected for transformation with the nucleotide of the present invention from those plants that are susceptible to the plant pathogen whose signaling gene in plants has been isolated.

The invention further enables transformation of plants with said nucleotide sequence or transformation of plant parts including plant parts required for the multiplication or reproduction of the plant.

Polypeptide products are also within the frame of the present invention, especially those polypeptide products that are defined as the product of the expression of a nucleotide sequence according to the invention.

Such a polypeptide product of the invention is the product being active in signal transduction in the defence of plants against a plant pathogen and being capable of interacting with a polypeptide encoded by said plant pathogen.

Preferably, such a polypeptide product of the invention is capable of interacting with the N-terminal or C-terminal part of the polypeptide product encoded by the I-2 resistance gene or is capable of interacting with at least part of with the polypeptide product of the Mi gene or with both.

Among the polypeptides capable of interacting with a polypeptide product encoded by a nucleotide sequence capable of hybridizing to the nucleotide sequence of the I-2-gene and/or the Mi-gene, the present invention encompasses those depicted as Interactor K-10, Interactor K-23, Interactor K-6, Interactor J-49 and/or Interactor S-25.

In an especially preferred embodiment, the present invention pertains to the use of Interactor S-25 (also called PP5) in modifying the defence mechanism of a plant against a plant pathogen.

According to the present invention, the nucleotide sequences are used for the activation of defence reactions against plant pathogens.

Accordingly, in a preferred embodiment the present invention pertains to the use of the presently claimed sequences and polypeptides in a method for influencing the signal transduction system in a plant in order to preferably exert influence on the resistance of plant against pathogens.

Accordingly, in a preferred embodiment the present invention pertains to the use of the presently claimed sequences and polypeptides in eliciting, inducing, activating, contributing, enhancing or (down) regulating to the resistance of plants to pathogens and more in particular to soil plant pathogens.

The nucleotides according to the present invention can be used in the activation of defence reactions in plant.

Preferably the nucleotides are used by cloning into the plants and preferably, but not necessarily in an antisense direction.

Plant that are transformed in order to express a defence reaction against plant pathogens include those plants that are cited in the examples and further include plants selected from higher plants, for example monocotyledon or dicotyledon plants, including species from the genera of *Avena, Agrostis, Antirrhinum, Arabidopsis, Asparagus, Atropa, Brassica, Beta, Bromuis, Browaalia, Capsicum, Ciahorum, Citrullus, Citrus, Composita, Cucumis, Cucurbita, Datura, Daucus, Digitalis, Festuca, Fragaria, Geranium, Glycine, Gramina, Helianthus, Heterocallis, Hordeum, Hyoscyamus, Juglans, Lactuca, Linum, Lolium, Lotus, Lycopersicon, Majorana, Manihot, medicago, Nemesis, Nicotiana, Onobrychis, Oryza, Panieum, Pelargonium, Pennisetum, Petunia, Phaseolus, Pisum, Ranunculus, Raphanus, Rosa, Salpiglossis, Secale, Senecio, Sinapis, Solanum, Sorghum, Trifolium, Trigonella, Triticum, Vigna, Vita* and *Zea*.

In a preferred embodiment of the invention, the plant is preferably solanacea, such as exemplified by tomato, eggplant, pepper, tobacco, potato and the like, more preferably tomato.

According to a particular embodiment of the invention, R-gene independent activation of defence is sought. To achieve this, three routes are presented.

The first route is by expressing the nucleotide sequences of interest, preferably of the present invention (the so-called signaling genes) using a pathogen inducible promoter. Expression of the downstream signaling component of the signaling pathway occurs at the site of the pathogen invasion with a different timing and at a higher level than normally (i.e. when pathogen invasion takes place without the additional use of the nucleotides sequences of the present invention). Depending on the promoter used, the localization of defence response results in resistance against foliar or root pathogens. Examples of a suitable promoter in this respect is Potato GST.

Another route is to engineer signaling genes with a conserved protein structure to either a dominant negative or constitutively active form. Mutations in conserved amino acid motifs that alter the biochemical properties of a protein have been described for many signaling components (Kinases, phosphatases, G-proteins, transcription factors etc.).

The third route, in case the interactor gene codes for a negative regulator of the defense response, is to achieve down-regulation of gene expression. Down-regulation of gene expression can advantageously be achieved in general by the use of interfering RNAs. Examples of such interfering RNAs are known in the art and examples thereof are amplicons, inverted repeat structures or dsRNAs. These interfering RNAs preferably lead to PTGS (Post Transcriptional Gene Silencing) and, consequently to down-regulation of the gene.

In theory, an interactor according to the invention functions as a component of the signal transduction pathway. Such a component can have two functions, activating (activator) or repressing (repressor). A component with a different function (activator or repressor) generally requires a different way of interfering with the signal transduction pathway. Modification of interactor functionality is desirable in order to achieve broad and durable disease resistance. In the case of an activator component modification of its functionality can be achieved through overexpression of the functional domain or the entire polypeptide. By this overexpression, the polypeptide encoded by said sequence will be formed in excess compared to the normal situation (i.e. in absence of overexpression) and will exert an influence on the signal transduction pathway. In case the interactors according to the invention have a repressor function, modification of the functionality can be achieved by down-regulation of its natural expression level, e.g. by antisense or interfering RNA technology which, for instance through PTGS, provide for the desired down-regulation. In the case of repressor used in an antisense orientation, the desired effect can be achieved by using functional homologues or functional fragments."

The combination of altered expression patterns and biochemical properties of common signaling genes is preferably applied. Because no specific recognition is required, breaking down of resistance is less likely to occur and hence provides for durable resistance.

DESCRIPTION OF THE FIGURES

FIGS. 1 to 5 represent nucleotide sequences and corresponding amino acid sequences of I-2 and/or Mi interactors. FIG. 1 includes SEQ ID NO: 1 (DNA) and SEQ ID NO: 2 (Protein). FIG. 2 includes SEQ ID NO: 3 (DNA) and SEQ ID NO: 4 (Protein). FIG. 3 includes SEQ ID NO: 5 (DNA) and SEQ ID NO: 6 (Protein), FIG. 4 includes SEQ ID NO: 7 (DNA) and SEQ ID NO: 8 (Protein). FIG. 5 includes SEQ ID NO: 9 (DNA) and SEQ ID NO: 10 (Protein).

FIGS. 1–3 (SEQ ID NOS: 1–6) represent nucleotide sequences of interactors that encode for polypeptide products that are capable of recognizing the N-terminal part of the I-2 polypeptide product and/or at least part of the Mi-polypeptide product.

FIGS. 4 and 5 (SEQ ID NOS: 7–10) represent nucleotide sequences of interactors that encode for polypeptide products that are capable of recognizing the C-terminal part of the I-2 polypeptide product and/or at least part of the Mi-polypeptide product.

Figure 7A:
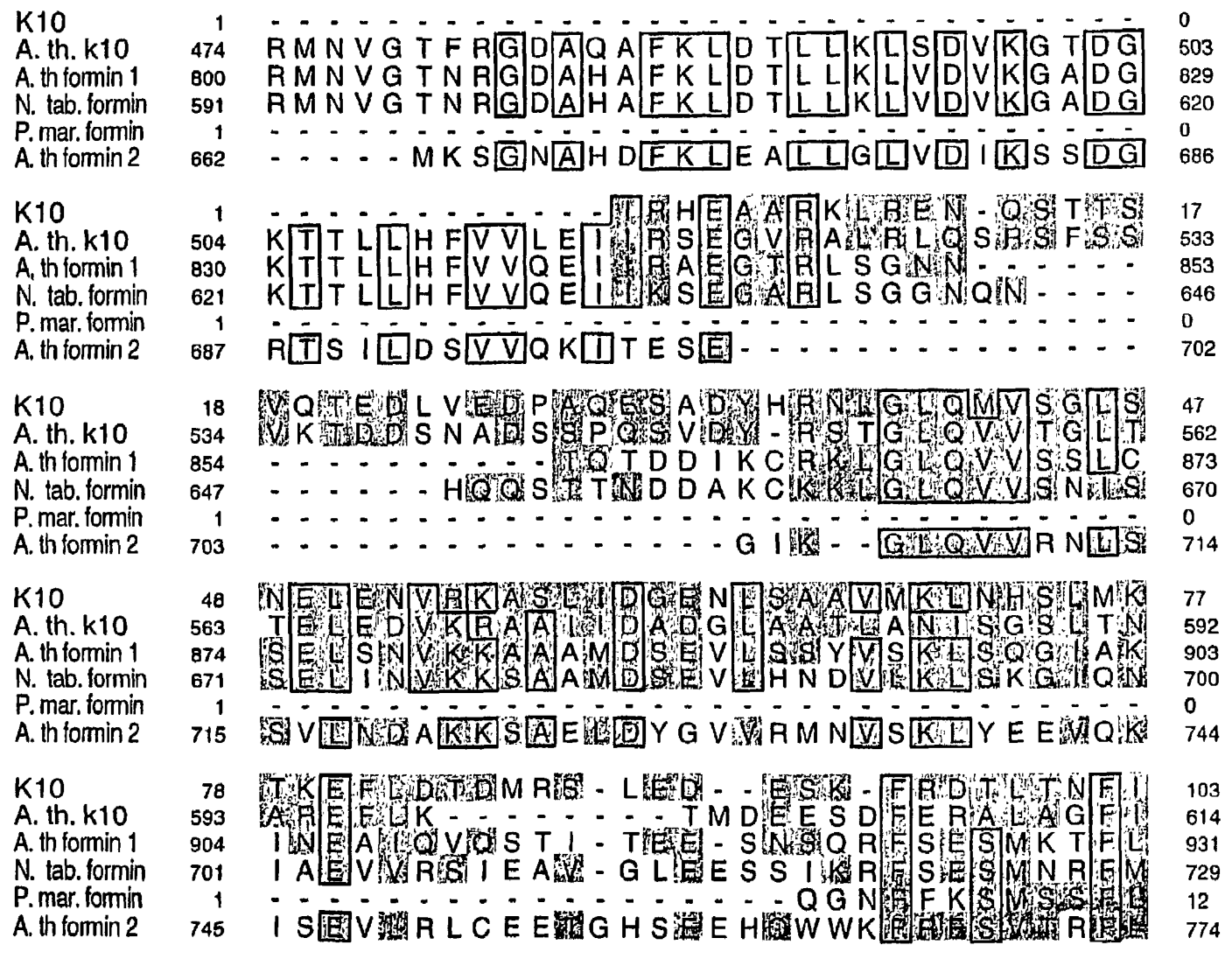

FIG. 7: Alignment of the protein sequence of clone K10 (SEQ ID NO: 15) with proteins from different plant origin. The Arabidopsis sequence K10 (SEQ ID NO: 16) was derived from accession number Z97338, the Arabidopsis forming 1 sequence (SEQ ID NO: 17) was derived from accession number AAF145548, the Nicotinia tabacum sequence (SEQ ID NO: 18) was derived from accession number AAF24497, the Picea mariana sequence (SEQ ID NO: 19) was derived from accession number AAC32145, the Arabidopsis forming 2 sequences (SEQ ID NO: 20) was derived from accession number AAF02158.

FIG. 8: Alignment of the protein sequence of clone K6 (SEQ ID NO: 21) with proteins from different plant origin. The Arabidopsis sequence K10 (SEQ ID NO: 22) was derived from accession number AAD20080 and the Oryza sativa sequence (SEQ ID NO: 23) was derived from accession number BAA90355.

FIG. 9: Alignment of the protein sequence of clone K23 (SEQ ID NO: 24) with different plant proteins. The Arabidopsis sequence KLC1 (SEQ ID NO: 25) was derived from accession numberT01892 and the Arabidopsis KLC2 sequence (SEQ ID NO: 26) was derived from accession number AAC80630.

FIG. 10: Alignment of the protein sequence of clone S25 (SEQ ID NO: 27) with an Arabidopsis protein sequence that was derived from accession number AAD21727.

Figure 6B:
FIG. 6: Alignment of the protein sequence of clone J49 (SEQ ID NO:29) with proteins from different plant origin. The soybean sequence (SEQ ID NO:11) was derived from accession number P04793, the Arabidopsis sequence (SEQ ID NO:12) was derived from accession number AAC95188, the Wheat (SEQ ID NO: 13) sequence was derived from accession number P12810, the Maize sequence (SEQ ID NO: 14) was derived from accession number S23212.

Other features and advantages of the invention are derivable from the examples and drawings.

EXPERIMENTAL PART

As a model for race specific recognition of pathogens by plants, the interaction between tomato (*Lycopersicon esculentum*) and the causal agent of *Fusarium* wilt, the fungus

*Fusarium oxysporum* was inevstigated. Tomato is the only host for the forma specialis (f.sp.) *lycopersici* of this worldwide occurring soil-borne pathogen. Three races of *F. oxysporum* (f.sp.) *lycopersici* (Fol) have been described. Interactions between isolates of races of Fol and tomato plants carrying various resistance genes have provided evidence for the so-called gene-for-gene relationship. (Mes et al., 1999). According to the gene-for-gene hypothesis (Flor et al., 1971; Keen, 1990), a pathogen-derived ligand (a race specific elicitor encoded by an avirulence gene) is recognized by a plant receptor encoded by a corresponding R-gene from the plant. Binding the elicitor activates the receptor or receptor complex. During this process, interactions of the receptor with other proteins are believed to occur, or components of the receptor complex may be dephosporylated. In this way an intracellular signal transduction cascade is triggered, leading to an efficient defence response (Staskawicz et al., 1995; Song et al., 1995).

The primary structures of the products of cloned R-genes seem to confirm the receptor-like character of these proteins (Staskawicz et al., 1995; Grant et al., 1995). With one exception (pto) all R-gene products contain an leucine rich repeat region (LRR). Leucine rich repeats in general are involved in protein-protein interactions. Low conservation is observed in the primary sequence but the three-dimensional structure is believed to be very similar. Such a variability enables the recognition of very diverse ligands, and therefor the LRR region is considered to be a receptor domain for pathogen derived ligands. Many R-gene products contain, besides a C-terminal LRR a central nucleotide binding site (NBS) and a variable N-terminus. The N-terminus is believed to cause the specificity of the downstream signaling. A set of R-gene products that contain a Leucine zipper (LZ) seem to activate the same signaling cascade. A different signaling cascade is activated by a set of R-gene products with a so-called TIR (Toll Interleukin receptor Related) domain in their N-termini (Aarts et al., 1998). The N-terminus of I-2 belongs to a new class that is characterized by a high percentage of charged amino acid residues.

Methodology

The yeast two-hybrid system (Field and SONG,1989; Gyuris et al., 1993) has been used to clone genes encoding proteins that physically interact with the I-2 gene product or with the Mi-gene product. In the following example, the two hybrid system proposed by CLONTECH under the name MATCHMAKER GAL4 has been used in accordance with the yeast protocol handbook and the MATCHMAKER vectors Handbook of the manufacturer.

The sequences encoding the 870 N-terminal amino acids (construct A) and the 750 C-terminal amino acids (construct B) of the I-2 protein were fused to the GAL4 binding domain (BD) in the yeast shuttle vector pAS2-1. The two fusion proteins were highly expressed in the yeast strain PJ69-4A, indicating that these strains were suitable for interaction cloning. A prey library was constructed in the (lambda) ACT-II vector (Memelink, J. et al. Elsevier Trends Journals Technical Tips Online, April 2000) using cDNA made from RNA isolated from stem and root tissue of a susceptible tomato cultivar that had been inoculated with Fol race 2. A saturated screen of this library in both yeast strains harboring the bait plasmids yielded five transformants that expressed all three marker genes (HIS3, LacZ, ADE2). This activation was confirmed to depend on the presence of the I-2 bait. Southern blotting revealed that all clones originated from tomato and not from the fungus. The inserts of the plasmids have been sequenced and all five clones showed homology to sequences in the database (see FIG. 1–5).

Interactors with the N-terminal Domain of I-2:

| | |
|---|---|
| Interactor K-10 (diaphanous/forming homolog) | (Seq. Id. No: 1–2) |
| Interactor K-23 (kinesin light chain homolog) | (Seq. Id. No: 3–4) |
| Interactor K-6 (Translin homolog) | (Seq. Id. No: 5–6) |

| | |
|---|---|
| Interactor J-49 (Hsp 17) | (Seq. Id. No: 7–8) |
| Interactor 2–25 (PP5, TPR-Phosphatase homolog) | (Seq. Id. No: 9–10) |

Figure 11:
FIG. 11: An overview of the interactors found when using the I-2 gene. The black lines indicate the domains of the I-2 protein with which the respective interaction clones were identified. K6 is a translin homologue of tomato. K10 is a formin homologue of tomato. K23 is kinesin light chain homologue. S25 is a type 5 protein phosphatase (PP5). J49 is a class 17 heat shock protein.

A schematic representation of the location of the bait domains correlating to identified interactor clones is given in FIG. 11.

Members of the PP5 are involved in receptor mediated signaling. Besides a C-terminal catalytical domain, members of this family contain four tetratricopeptide repeat (TPR) motifs. This domain has a regulatory function since binding of arachidonic acid to this domain increases the phosphatase activity 25-fold in mammalian cells (Chen and Cohen 1997), In addition, there is evidence that TPR domains are involved in interactions with other proteins.

To demonstrate that different R-genes make use of the same signal transduction components, the present invention shows that that clone S-25 also binds to the Arabidopsis RPM1 protein in the yeast two-hybrid system and to the tomato LRR domain of the tomato Mi-protein.

Conclusive evidence that even distantly related plants have similar signal transduction components is provided by the finding that for all clones homologs have been found in Arabidopsis. Accordingly, the application of the presently found interactors in a wide range of crop plants to interfere with the signal transduction system for the generation of resistance is demonstrated.

Application of the Isolated Interactor Genes in Obtaining Broad Resistance Tolerance Antisense Expression of Interactors in Resistant and Susceptible Tomato To investigate the role of the interactors of the present invention in the defense response, 35S::antisense interactor constructs have been generated (b21, b23, b25 and b60). As a silencing control antisense I-2 is used (b27). These antisense constructs have been introduced into the *Fusarium oxysporum* race two resistant cultivars Mogeor and the *Fusarium oxysporum* race 2 sensitive cultivar RZ52201. From both cultivar/construct combinations approximately 50 plants were regenerated after *Agrobacterium* mediated transformation of cotyledons. Diploid plants were identified by counting the number of amyloplasts in the stomatal guard cells (results are shown in Table 1).

Approximately 35 diploid plants of each cultivar/construct combination were selected for further analysis.

The selected diploid plants were tested for the presence of the transgene. Using a sense primer in the 35S promoter and an antisense primer in the nos transcriptional terminator, the transgene was specifically amplified by PCR from genomic DNA (results are shown in Table 2). Approximately 25 diploid and transgenic plants of each cultivar/construct combination were selected for further analysis.

TABLE 1

Distribution of the ploidy number in regenerated plants.

| Construct | plants counted # | RZ52201 diploid plants # | Diploid plants % | plants counted # | Mogeor diploid plants # | diploid plants % |
|---|---|---|---|---|---|---|
| b21 (as formin) | 60 | 33 | 55 | 52 | 32 | 62 |
| B23 (as kinesinLC) | 50 | 33 | 66 | 49 | 39 | 80 |
| b25 (phosphatase) | 50 | 42 | 84 | 48 | 37 | 77 |
| B27 (as I-2) | 52 | 41 | 79 | 49 | 35 | 71 |
| B60 (as translin) | 50 | 36 | 72 | 51 | 36 | 71 |
| LPR I-2::GUS::Nos | 0 | 0 | 0 | 12 | 12 | 100 |
| Total | 262 | 185 | 71 | 261 | 191 | 73 |

(as: antisense)

TABLE 2

Distribution of the presence of the transgene in diploid plants.

| Construct | plants PCR'd # | RZ52201 transgenic plants # | transgenic plants % | plants PCR'd # | Mogeor Transgenic plants # | transgenic plants % |
|---|---|---|---|---|---|---|
| b21 as formin | 33 | 25 | 76 | 32 | 26 | 81 |
| b23 as kinesin LC | 33 | 31 | 94 | 39 | 33 | 85 |
| b25 as phosphatase | 40 | 30 | 75 | 36 | 30 | 83 |
| b27 as I-2 | 37 | 31 | 84 | 35 | 29 | 83 |
| b60 as translin | 36 | 29 | 81 | 32 | 28 | 88 |
| LPR I-2::GUS::Nos | 0 | 0 | 0 | 12 | 11 | 92 |
| Total | 179 | 146 | 82 | 186 | 157 | 84 |

(as: antisense)

The PP5 mRNA levels were detected using a strand specific probe, thereby allowing the level of expression of the endogenous PP5 in the transgenic plants to be compared with the level in non-transgenic plants. Glyceraldehydefosfodehydrogenase was used as a loading control. Using a phosphor imager, the levels of expression as a percentage of the non-transgenic plant was calculated. Half of the Mogeor transgenes and one third of the RZ52201 transgenes showed less than 50% of the non-transgenic expression level.

The mRNAs of the other interactors were visualized on a Northern blot. The conditions for RNA detection were optimized and this resulted detection of the Translin (K6) and Kinesin Light Chain (K23) mRNA. It has been demonstrated that Kinesin light chain appears to be specifically expressed in stem tissue as can be concluded from Northern results on RNA samples from different organs. Gene silencing of kinesin light chain can be assayed in stems from lateral shoots from transgenic plants.

Translin gene silencing was tested in mRNA of total lateral shoot tissue of the transgenic plants. The results show that 14% of the Mogeor transgenes and 27% of the RZ52201 transgenes showed less than 50% of the non transgenic expression level.

All transgenic plants were grown to maturity and were self-fertilized. The resulting R1 seed were subjected to disease assays as described below. Because R1 seedlings are tested, the expected segregation of the transgene is 1:2:1 for non-transgenic:heterozygous:homozygous.

Suppression of Resistance to *Fusarium oxysporum* f.sp. *lycopersici* Race 2 in Resistant Plants Antisense interactor expressing lines of the *Fusarium oxysporum* race 2 resistant tomato cultivar Mogeor were investigated for loss or reduction of the resistance response against *Fusarium* race 2. A line expressing the antisense I-2 gene was included as a control to measure the effectivity of antisense suppression on the disease response. These experiments are based on the assumption that the interactors are positive regulators of the disease response. The alternative assumption, stating that interactors act as negative regulators of the disease response, was tested by antisense expression in the susceptible tomato cultivar RZ52201 and is described here-in be.

The disease response was tested by inoculating a population of 20 seedlings per transgenic line with Fusarium oxysporum race 2 and with water as a control for variability in plant weight. Three weeks after inoculation the plants were weighed and a disease index was given to each plant.

Disease Symptoms were Indexed as Follows:

0: healthy plant
1: disease symptoms but no vessel browning (just below cotyledons)
2: 1 or 2 brown vessels (just below cotyledons)
3: 3 or more brown vessels (just below cotyledons)
4: completely wilted plant Based on these parameters it is determined if disease resistance is affected. The segregation of diseased and healthy plants is determined in the population of 20 plants tested for each line. These data are shown in Table 3.

Four out of five anti-sense I-2 lines of Mogeor (Table 3) showed reduced disease resistance to *Fusarium* race 2 and hence silencing is efficiently induced by the antisense expression.

TABLE 3

Effect of antisense I-2 expression in Mogeor. 'Mogeor NT' is the non-transgenic Mogeor plant.

| Line | disease resistance affected | Number of diseased plants |
|---|---|---|
| Mogeor-NT |  | 0 |
| M27-26 | + | 12 |
| M27-31 | + | 12 |
| M27-35 | − | 0 |
| M27-36 | + | 7 |
| M27-39 | + | 14 |
| M27-48 | + | 14 |

Increase in tolerance to *Fusarium oxysporum* f. sp. *lycopersici* race 2 in susceptible plants The identified interactor genes may act as negative regulators of the disease response. This is tested by investigating the disease response in transgenic lines of a susceptible cultivar (RZ52201) expressing the antisense interactor genes, and evaluating increase in disease tolerance.

Again, 20 seedlings per transgenic line were inoculated with *Fusarium oxysporum* race 2 and with water as a control for variability in plant weight. Three weeks after inoculation the plants were weighed and a disease index was given to each plant as described herein-before.

TABLE 4

Effect of anti-sense PP5 phosphatase expression in RZ52201 on tolerance to *Fusarium oxysporum* race 2. 'RZ52201' is the non-transgenic RZ52201 plant. The 'disease index' is the average of the index scores for each individual seedling per transgenic line. The 'ratio infected weight over water weight' is the average seedling weight 3 weeks after inoculation with Fusarium race 2 over the average weight of water-treated controls, expressed as a percentage.

| Line | disease resistance affected | disease index | ratio infected weight over water weight (%) | # of healthy plants (disease index 0 or 1) per 20 seedlings |
|---|---|---|---|---|
| RZ52201 | | 3.35 | 26 | 0 |
| KG25-20 | − | 2.45 | 52 | 4 |
| KG25-22 | + | 2.37 | 44 | 5 |
| KG25-23 | − | 3.42 | 31 | 2 |
| KG25-26 | + | 2.35 | 48 | 5 |
| KG25-28 | − | 3.25 | 37 | 0 |

TABLE 4-continued

Effect of anti-sense PP5 phosphatase expression in RZ52201 on tolerance to *Fusarium oxysporum* race 2. 'RZ52201' is the non-transgenic RZ52201 plant. The 'disease index' is the average of the index scores for each individual seedling per transgenic line. The 'ratio infected weight over water weight' is the average seedling weight 3 weeks after inoculation with Fusarium race 2 over the average weight of water-treated controls, expressed as a percentage.

| Line | disease resistance affected | disease index | ratio infected weight over water weight (%) | # of healthy plants (disease index 0 or 1) per 20 seedlings |
|---|---|---|---|---|
| KG25-29 | − | 3.21 | 23 | 0 |
| KG25-30 | − | 2.85 | 42 | 1 |
| KG25-34 | − | 3.55 | 25 | 0 |
| KG25-35 | + | 2.25 | 76 | 5 |
| KG25-36 | − | 2.60 | 47 | 4 |
| KG25-37 | + | 2.10 | 78 | 4 |
| KG25-38 | − | 2.47 | 48 | 4 |
| KG25-40 | + | 2.32 | 39 | 6 |
| KG25-41 | − | 2.42 | 48 | 4 |
| KG25-42 | + | 1.65 | 82 | 11 |
| KG25-43 | + | 2.05 | 37 | 8 |
| KG25-44 | − | 2.79 | 44 | 2 |
| KG25-46 | − | 3.45 | 23 | 0 |
| KG25-47 | + | 2.11 | 47 | 2/10 |

None of the antisense translin lines of RZ52201 induced a significant increase in resistance. Seven out of eighteen antisense PP5 phophatase lines of RZ52201 showed a significant increase in disease resistance (Table 4). Five out of these seven resistant lines showed silencing in the R0 generation (primary transformants). There is a correlation between silencing and disease resistance. Suppression of expression of the interactor gene encoding PP5 phosphatase increases the tolerance to *Fusarium* race 2 in a susceptible tomato line. Based on the data in Table 2, PP5 is a negative regulator of defence against *Fusarium* race 2. To support this notion, a correlation should be found between silencing of the endogenous PP5 gene and the observed resistance in the T1 population.

The correlation between silencing and disease resistance in T1 populations of antisense PP5 in RZ52201 plants.

In order to demonstrate that PP5 is constitutively expressed and not influenced by fungal infection, 10-day-old seedlings of non-transgenic plants were inoculated with *Fusarium oxysporum* race 2. RNA was isolated from these plants 21 days post inoculation, and hybridised against a PP5 probe. The results showed that PP5 is expressed constitutively. Accordingly infected transgenic plants were tested for silencing of PP5. 10-day-old T1 seedlings of transgenic plants KG25-26 and KG25-42 were inoculated with *Fusarium oxysporum* race2. RNA was isolated from these plants 21 days post-inoculation. Also genomic DNA was isolated from these plants and successively digested with EcoRI in order to show the presence of the T-DNA. All plants containing the T-DNAs showed silencing of the endogenous PP5 gene. Four out of seven silenced plants were tolerant to *Fusarium.*

Based on this finding and on the finding that PP5 can bind to multiple R-genes, we chose to focus on PP5 transgenic plants.

Increase in Tolerance to *Fusarium oxysporum* f.sp. *lycopersici* Race 3 in Susceptible Plants Race 3 of *Fusarium oxysporum* f.sp. *lycopersici* differs from race 2 in its ability to infect tomato plants that carry the I-2 R-gene. The I-2 gene does not confer resistance to race 3. The tomato genotype Mogeor is susceptible to race 3 of *Fusarium*. It was tested whether antisense suppression of PP5 in this susceptible tomato line increases tolerance to race 3, apart from the above mentioned effects on tolerance to race 2.

Seedlings of a number of antisense PP5 lines of RZ52201 were inoculated with *Fusarium oxysporum* race 3 using the procedure described above. Three weeks after inoculation the seedlings of each line were analyzed for plant weight and and disease index. The results are summarized in Table 5. Eight out of thirteen lines tested showed an increase in tolerance to infection with *F. oxysporum* race 3.

TABLE 5

Effect of anti-sense PP5 phosphatase expression in Mogeor on tolerance to *Fusarium oxysporum* race 3. 'Mogeor' is the non-transgenic Mogeor plant. The 'disease index' is the average of the index scores for each individual seedling per transgenic line.

| Line | disease resistance affected | Disease index | seedling weight (g) | # of healthy plants (disease index 0 or 1) per 20 seedlings |
|---|---|---|---|---|
| Mogeor |  | 2.85 | 1.48 | 1 |
| M25-03 |  | 3.20 | 2.00 | 3 |
| M25-06 | + | 2.25 | 3.65 | 6 |
| M25-07 | + | 1.68 | 3.85 | 10 |
| M25-08 |  | 3.15 | 2.44 | 1 |
| M25-16 | + | 1.75 | 5.01 | 7 |
| M25-23 |  | 2.75 | 2.54 | 3 |
| M25-26 |  | 3.05 | 2.61 | 1 |
| M25-32 | + | 2.13 | 2.41 | 5 out of 15 |
| M25-36 | + | 2.35 | 2.48 | 6 |
| M25-37 |  | 3.00 | 2.23 | 2 |
| M25-39 | + | 1.80 | 3.19 | 10 |
| M25-40 | + | 1.55 | 4.05 | 9 |
| M25-41 | + | 1.55 | 4.52 | 9 |

The effect of antisense suppression of PP5 in another susceptible tomato line, RZ52201, on the tolerance to *F. oxysporum* race 3 was tested. Six transgenic lines were chosen for this test, that already had shown increase in tolerance to race 2 in tests described above. These lines were tested for tolerance to race 3 alongside the appropriate controls, comparable to that described above for Mogeor. The controls consisted of both susceptible lines Mogeor and RZ52201. All six antisense RZ52201 lines showed an increase in tolerance to infection with race 3 (Table 6).

TABLE 6

Effect of anti-sense PP5 phosphatase expression in RZ52201 on tolerance to *Fusarium oxysporum* race 3. 'Mogeor' and RZ52201 are non-transgenic susceptible control lines. The 'disease index' is the average of the index scores for each individual seedling per transgenic line. The 'ratio infected weight over water weight' is the average seedling weight 3 weeks after inoculation with Fusarium race 2 over the average weight of water-treated controls, expressed as a percentage.

| Line | disease resistance affected | Disease index | ratio infected weight over water weight (%) | # of healthy seedlings (disease index 0 or 1) per total seedlings |
|---|---|---|---|---|
| Mogeor | − | 3.50 | 13.3 | 1/10 |
| RZ52201 | − | 3.78 | 3.3 | 0/9 |
| KG25-26 | + | 3.10 | 23.3 | 1/10 |
| KG25-37 | + | 2.20 | 75.3 | 6/20 |
| KG25-40 | + | 2.79 | 30.7 | 4/19 |
| KG25-42 | + | 2.90 | 35.2 | 1/10 |
| KG25-43 | + | 2.65 | 38.5 | 4/20 |
| KG25-47 | + | 1.95 | 66.4 | 6/19 |

Increase in tolerance to *Verticillium dahliae* in susceptible tomato plants

The six antisense PP5 tomato lines of cultivar RZ52201, that had shown increased tolerance to both races 2 and 3 of *Fusarium oxysporum*, were now subjected to a *Verticillium* disease assay. The assay was performed in a comparable manner as described for *Fusarium*. For this assay, RZ52201 was included as a susceptible control, whereas the line Mogeor, which carries the tomato Ve gene and is resistant to *Verticillium* infection, was used as a resistant control.

Four out of the six antisense lines showed an increased tolerance to infection with *Verticillium dahliae* (Table 6). These results demonstrate that at least four transgenic tomato lines could be identified, in which the downregulation of PP5 expression through antisense resulted in a significant increase in tolerance to at least three different fungal pathogens: races 2 and 3 of *Fusarium oxysporum* and *Verticillium dahlia*. In these cases, a significant number of plants out of all seedlings tested showed a disease index of either 0 or 1, which is considered to be resistant or tolerant.

TABLE 7

Effect of anti-sense PP5 phosphatase expression in RZ52201 on tolerance to Verticllium dahliae. 'Mogeor' and RZ52201 are non-transgenic susceptible control lines. The 'disease index' is the average of the index scores for each individual seedling per transgenic line. The 'ratio infected weight over water weight' is the average seedling weight 3 weeks after inoculation with Fusarium race 2 over the average weight of water-treated controls, expressed as a percentage.

| Line | disease resistance affected | disease index | ratio infected weight over water weight (%) | # of healthy seedlings (disease index 0 or 1) per total seedlings |
|---|---|---|---|---|
| Mogeor | + | 0.70 | 74 | 9/10 |
| RZ52201 | − | 2.78 | 40 | 0/9 |
| KG25-26 | + | 2.20 | 48 | 3/20 |
| KG25-37 | − | 2.50 | 41 | 0/20 |
| KG25-40 | − | 2.70 | 23 | 2/20 |
| KG25-42 | + | 1.80 | 57 | 5/20 |
| KG25-43 | + | 1.95 | 33 | 5/20 |
| KG25-47 | + | 2.00 | 57 | 5/20 |

All of the populations tested above consisted of seed batches of R1 seed of transgenic lines, obtained after selfing of the primary transformants. In the R1 generation, the single copy antisense transgene will segregate in a 1:2:1 manner for homozygous absent : heterozygous : homozygous present. Thus on average 25% of the seedlings tested will not be affected in their disease response as they carry no antisense PP5 gene. The strongest effects of the suppression of PP5 will be expected in on average 25% of the seedlings, which are homozygous for the transgene. In many of the examples above a good tolerance (disease index 0 or 1) was observed in 5 or 6 individuals out of 20, which correlates well to the prediction of Mendelian segregation.

Tolerance to *Clavibacter michiganensis* in Susceptible Tomato Plants

Antisense PP5 lines of both Mogeor and RZ52201 were tested for tolerance to *Clavibacter michiganesis* subsp. *michiganesis* (bacterial cancer). Both parental tomato cultivars are susceptible to this pathogen, resulting in wilting and vascular discoloration. Seedlings were infected with a spore suspension of the bacterial pathogen and replanted in soil. At regular intervals over 6 weeks the individuals showing wilting symptoms were scored and removed. Individual plants were considered resistant when at the end of five weeks, at which point all controls were clearly affected by the disease, they were symptomless. Twelve out of 23 antisense lines, mostly of the genotype Mogeor, showed a significant number of resistant individuals after 5 weeks, whereas the susceptible controls showed none. Two of the RZ52201 lines containing resistant individuals, KG25-22 and KG25-43, had previously been identified as having increased tolerance to *Fusarium oxysporum* race 2.

TABLE 8

Tolerance to infection with Clavibacter in antisense PP5 expressing tomato plants. The individual offspring plants of 23 antisense lines were scored for resistance or symptom formation four weeks after inoculation. Nine out of 23 lines show individuals scored as resistant.

| Clavibacter | susceptible | resistant | % res | Increased Tolerance | # of plants tested |
|---|---|---|---|---|---|
| M25-03 | 23 | 1 | 4% | | 24 |
| M25-06 | 18 | 6 | 25% | + | 24 |
| M25-08 | 23 | 1 | 4% | | 24 |
| M25-16 | 21 | 3 | 13% | + | 24 |
| M25-23 | 16 | 2 | 11% | + | 18 |
| M25-26 | 21 | 3 | 13% | + | 24 |
| M25-32 | 15 | 3 | 17% | + | 18 |
| M25-36 | 20 | 4 | 17% | + | 24 |
| M25-39 | 21 | 3 | 13% | + | 24 |
| M25-40 | 14 | 10 | 42% | + | 24 |
| M25-48 | 16 | 8 | 33% | + | 24 |
| KG25-03 | 18 | 0 | 0% | | 18 |
| KG25-08 | 24 | 0 | 0% | | 24 |
| KG25-14 | 24 | 0 | 0% | | 24 |
| KG25-22 | 22 | 2 | 8% | + | 24 |
| KG25-26 | 24 | 0 | 0% | | 24 |
| KG25-38 | 23 | 1 | 4% | | 24 |
| KG25-40 | 23 | 1 | 4% | | 24 |
| KG25-42 | 23 | 1 | 4% | | 24 |
| KG25-43 | 22 | 2 | 8% | + | 24 |
| KG25-46 | 22 | 2 | 8% | + | 24 |
| KG25-47 | 23 | 1 | 4% | | 24 |
| KG25-49 | 17 | 1 | 6% | | 18 |
| susc. control | 66 | 0 | 0% | | 66 |

Tolerance to infection with *Meloidogyne incognita* in susceptible tomato plants Antisense PP5 lines of RZ52201 were tested for tolerance to infection with *Meloidogyne incognita* (root-knot nematode). The parental tomato cultivar RZ52201 is susceptible to infection with this pathogen, resulting in abundant root-knot formation and ultimately wilting of the plants. Seedlings at the 3 leaf stage were planted in soil contaminated with *Meloidogyne*. After four weeks, the individual plants were removed from the soil and analyzed for the formation of root-knots. The number of root-knots is scored in classes of 0 (resistant), 1–5, 5–1200 and >100. Various resistant controls, among which the cultivar Mogeor carrying the Mi gene, were included in the assay. From biochemical analysis underlying this invention it had previously been established that the interactor protein PP5 also binds to the LRR domain of the gene product of the tomato root-knot nematode R-gene Mi. Therefore, suppression of PP5 expression in tomato lines is expected to have an effect on the response to *Meloidogyne* infection.

Four out of 10 lines showed a significant higher number of plants with no root-knots at all over the susceptible controls. In transgenic line KG25-43 even >40% of individuals remained free of root-knot formation. Of these lines, KG25-26, KG25-42 and KG25-43 also showed increased tolerance to both races of *Fusarium* and to *Verticillium*. KG25-43, in addition, was also tolerant to *Clavibacter michiganensis*.

TABLE 9

Tolerance to infection with the root-knot nematode *Meloidogyne incognita* in antisense PP5 expressing tomato plants. The number of root-knots per plant was scored on offspring seedlings for each of 10 antisense lines. The numbers KG25-22, KG25-26, KG25-42 and KG25-43 show a significant increase in individuals resistant to root-knot formation over the susceptible control.

| | number of root-knots per plant | | | | total tested | % 0 | increased tolerance |
|---|---|---|---|---|---|---|---|
| Meloidogyne | 0 | 1–5 | 5–100 | >100 | | | |
| KG25-03 | 0 | 4 | 14 | 0 | 18 | 0% | |
| KG25-16 | 0 | 4 | 9 | 1 | 14 | 0% | |
| KG25-22 | 4 | 11 | 3 | 0 | 18 | 22% | + |
| KG25-26 | 5 | 5 | 6 | 0 | 16 | 31% | + |
| KG25-35 | 2 | 8 | 5 | 0 | 15 | 13% | |
| KG25-37 | 2 | 11 | 9 | 0 | 22 | 9% | |
| KG25-38 | 2 | 3 | 9 | 5 | 19 | 11% | |
| KG25-40 | 0 | 4 | 14 | 0 | 18 | 0% | |
| KG25-42 | 5 | 6 | 5 | 0 | 16 | 31% | + |
| KG25-43 | 8 | 8 | 2 | 0 | 18 | 44% | + |
| RZ52201 control | 1 | 4 | 3 | 0 | 8 | 13% | |
| Resistant controls | 14 | 0 | 0 | 0 | 14 | 100% | |

Tolerance to infection with Tomato Spotted Wilt Virus in susceptible tomato plants Eleven antisense PP5 lines of the tomato cultivar Mogeor were tested for tolerance to infection with Tomato Spotted Wilt Tospovirus (TSWV). Leaves of young seedlings at a two-leaf stage were lightly dusted with carborundum powder and subsequently infected by applying a crude cell extract of a severely diseased tomato plants previously infected with TSWV. The plants were analyzed for symptoms of TSWV infection 14 days post-inoculation and scored 'resistant' or 'susceptible'. Included in the assay were the non-transformed line Mogeor and a number of other susceptible varieties (GT and RZ52201) as susceptible controls. In nine out of eleven antisense lines, a higher number of resistant individuals was observed than in the susceptible control Mogeor. Lines with ≧25% of individuals scored as 'resistant' were regarded as having a significantly increased tolerance to infection with this virus. Thus 5 lines were identified in which the antisense suppression of PP5 resulted in a significant increase in tolerance (Table 10).

TABLE 10

Tolerance to infection with Tomato Spotted Wilt Virus (TSWV) in antisense PP5 expressing tomato plants. The individual offspring plants of 23 antisense lines were scored 'resistant' or 'susceptible'. Ten out of 23 lines show significantly higher numbers of individuals scored as resistant to TSWV over the susceptible controls.

| TSWV test | resistant | Susceptible | # of tested plants | % resistant | increased resistance |
|---|---|---|---|---|---|
| M25-03 | 9 | 15 | 24 | 38% | + |
| M25-06 | 6 | 18 | 24 | 25% | + |
| M25-08 | 5 | 19 | 24 | 21% | |
| M25-16 | 5 | 19 | 24 | 21% | |
| M25-23 | 6 | 12 | 18 | 33% | + |
| M25-26 | 1 | 23 | 24 | 4% | |
| M25-32 | 1 | 17 | 18 | 6% | |
| M25-36 | 5 | 19 | 24 | 21% | |
| M25-39 | 3 | 21 | 24 | 13% | |
| M25-40 | 7 | 11 | 18 | 39% | + |
| M25-48 | 9 | 15 | 24 | 38% | + |
| susc. Control | 0 | 42 | 42 | 0% | |
| Mogeor | 4 | 20 | 24 | 17% | |

Tolerance to infestation with potato aphid in susceptible tomato plants

Twelve antisense PP5 lines of RZ52201 were tested for tolerance to infestation with potato aphid (*Macrosiphum euphorbiae*). Individual seedlings of each line were inoculated with 10–15 adult female aphids per plant. After 2½ weeks, the individual plants were scored for the presence of colonizing aphid populations. Plants were regarded as 'resistant', 'lightly susceptible' or heavily susceptible' as follows:
resistant: no aphid multiplication has occurred (the number of aphids per plants corresponded approximately to the number initially inoculated),
lightly susceptible: the aphid population has increased 1.5 to 2.5 fold in numbers,
heavily susceptible: the aphid population has multiplied several fold in numbers, resulting in the entire plant being covered with aphids.

A number of antisense lines show significant higher numbers of individuals scored as 'resistant' compared to the susceptible control. Lines in which 30% or more of individual seedlings were scored as 'resistant' were regarded to have an increased tolerance to aphid infestation. Four lines were thus identified with increased tolerance (Table 10). The highest resistance score was obtained with antisense line KG25-43 with 45% of individuals remaining resistant to aphid infection. This particular line had also been identified as having increased tolerance to all other pathogens tested (both races of *Fusarium oxysporum*, *Verticillium*, nematodes and *Clavibacter michiganensis*).

The results of the disease tests performed with antisense PP5 lines of either Mogeor or RZ52201 clearly show that antisense suppression of the expression of the PP5 gene in these lines results in significantly increased tolerance to a broad range of pathogens, including plant viruses, plant pathogenic bacteria and fungi, nematodes and aphids. It should be kept in mind, that in all cases the plant populations tested consisted of R1 generations, in which the transgene segregates and the effects of the transgene on disease tolerance is not expected to occur in 100% of the individuals tested. Also, as is well known in the state of the art, antisense suppression of gene expression results in a range of the degree of reduction of gene expression. Within a population of plants transformed with an antisense construct, only a small proportion of lines will show an almost complete silencing of gene expression, whereas other lines will have various degrees of reduction in expression. Thus, it is expected that within the antisense populations tested, a number of lines show a clear increase in disease tolerance, whereas other lines do less so or not at all.

A number of antisense lines showed a strong increase in tolerance to most or all pathogens tested. In particular, antisense lines KG25-43 was identified as having increased tolerance in disease tests of both races 2 and 3 of *Fusarium oxysporum*, *Verticillium dahliae*, *Meloidogyne incognita*, *Macrosiphum euphorbiae* and *Clavibacter michiganensis*. In antisense lines of Mogeor, which parental line already contains a number of resistance genes, only tests to TSWV and *F. oxysporum* race 3 were performed. In these populations, two lines were identified having increased tolerance to both these pathogens.

TABLE 11

Tolerance to infestation of potato aphid *Macrosiphum euphorbiae* in antisense PP5 expressing tomato plants. The individual offspring plants of 12 antisense lines were scored 'resistant', 'lightly susceptible' or 'heavily susceptible'. The numbers KG25-08, KG25-14, KG25-43 and KG25-49 show significantly higher numbers of individuals scored as resistant to aphid infestation over the susceptible control.

| M. Euphorbiae | resistant | lightly susceptible | heavily susceptible | # of plants | % res | increased tolerance |
|---|---|---|---|---|---|---|
| KG25-03 | 2 | 10 | 10 | 22 | 9% | |
| KG25-08 | 6 | 13 | 1 | 20 | 30% | + |
| KG25-14 | 6 | 11 | 3 | 20 | 30% | + |
| KG25-22 | 0 | 14 | 6 | 20 | 0% | |
| KG25-26 | 3 | 13 | 4 | 20 | 15% | |
| KG25-38 | 3 | 15 | 2 | 20 | 15% | |
| KG25-40 | 0 | 11 | 9 | 20 | 0% | |
| KG25-42 | 2 | 16 | 2 | 20 | 10% | |
| KG25-43 | 9 | 7 | 4 | 20 | 45% | + |
| KG25-46 | 2 | 12 | 6 | 20 | 10% | |
| KG25-47 | 3 | 10 | 7 | 20 | 15% | |
| KG25-49 | 6 | 10 | 4 | 20 | 30% | + |

TABLE 11-continued

Tolerance to infestation of potato aphid *Macrosiphum euphorbiae* in antisense PP5 expressing tomato plants. The individual offspring plants of 12 antisense lines were scored 'resistant', 'lightly susceptible' or 'heavily susceptible'. The numbers KG25-08, KG25-14, KG25-43 and KG25-49 show significantly higher numbers of individuals scored as resistant to aphid infestation over the susceptible control.

| M. Euphorbiae | resistant | lightly susceptible | heavily susceptible | # of plants | % res | increased tolerance |
|---|---|---|---|---|---|---|
| Susc. Control | 4 | 4 | 11 | 19 | 21% | |
| Resistant control | 18 | 2 | 0 | 20 | 90% | |

I-2 Interactor PP5 also interacts with domains of the tomato nematode R-gene Mi

The tomato R-gene Mi-1.2 confers resistance to infection with root-knot nematodes of the genus *Meloidogyne*. This gene was originally identified in *Lycopsericon peruvianum* and had been introgressed through breeding into a large number of modern tomato varieties. The gene has been isolated from tomato and cloned using a map-based cloning strategy in previous years. The Mi-1.2 gene belongs to the family of plant R-genes, because its gene product contains a leucine rich repeat (LRR) and a nucleotide binding site domain (NBS). The N-terminal domain of the Mi-1.2 gene product contains a so called TIR domain, and differs in this respect from the I-2 gene product. Also, it has been demonstrated that Mi-1.2 has a dual resistance specificity, in that this same gene also confers resistance to potato aphid (*Macrosiphum euphorbiae*), a plant pest that is totally unrelated to root-knot nematodes.

In order to investigate whether the I-2 Interactor protein PP5 is also capable of biochemical interactions with domains of the Mi-1.2 gene product, a number of bait vectors for yeast two-hybrid screening were constructed containing the LRR domain of the Mi-1.2 gene product, and the larger NBS-LRR domain. In a yeast two-hybrid assay both Mi domains showed a clear interaction with the PP5 interactor protein, indicating that the interaction of PP5 with the LRR domain of R-genes is not specific for the I-2 R-gene, but instead is a more general phenomenon.

The interaction of the PP5 clone with the LRR domain of Mi-1.2 is temperature dependent. The interaction occurs strongly at temperatures of 23° C., whereas at 30° C. interaction no longer occurs. This temperature effect has not been observed in the interaction of PP5 with the LRR domain of I-2, and must thus be explained by a temperature-dependent change in interaction capacity of the Mi-1.2 LRR domain. Indeed, from experience in tomato breeding and culture over several years, it is known that the Mi-1.2 gene confers resistance to root-knot nematodes and aphids in a temperature-dependent manner. At temperatures of 23–25° C. tomato plants carrying the Mi-1.2 gene are resistant to root-knot nematodes, whereas at temperatures of 30° C. the resistant phenotype is lost.

REFERENCES

Aarts N., Metz. M., Holub E. B., Staskawicz B. J., Daniels, M. D. and Parker J. E., (1998) Different requirements for EDS1 And NDR1 by disease resistance genes define at least two R gene mediated signaling pathways in Arabidopsis. Proc. Nat. Acad. Sci. USA 95: 10306–10311

Beffa R., Szell M., Meuwly P., Pay A., Vogeli-Lange R., Metraux J. P., Neuhaus G., Meins Jr F., Nagy F., (1995). Cholera toxin elevates pathogen resistance and induces pathogenesis-related gene expression in tobacco. EMBO J. 14: 5753–5761.

Bourne H. R., Sanders D. A., and McCormick F. (1991). The GTPase superfamily: conserved structure and molecular mechanism. Nature 349: 117–127.

Brunner D. Oellers N., Szabad J., Biggs $3^{rd}$ W. H., Zipursky S. L. and Hafen E. (1994). a gain of function mutation in Drosophila MAP kinase activates multiple receptor tyrosine kinase signaling pathways. Cell 76:875–888.

Claret F. X., Hibi M., Dhut S., Toda T., and Karin M. (1996). A new group of conserved coactivators that increase the specificity of AP-1 transcription factors. Nature 383: 453–457.

Chen S. Y., Huff S. Y., Li C. C., Der S., and Powers C. J. (1994). Rs 15-A protein shares highly similar dominant-negative biological properties with Ras-17N and forms a stable guanine-nucleotide resistant complex with CDC25 exchange factor. Oncogene: 9, 2691–2698.

Chen M. X. and Cohen P. T. W. (1997) Activation of protein phosphatase 5 by limited proteolysis or the binding of polyunsaturated fatty acids to the TPR domain. FEBS Lett. 400, 136–140.

Field S. and Song O. (1989) A novel genetic system to detect protein-protein interactions. Nature 340: 245–246.

Flor H. H., (1971). Current status of gene-for-gene concept. Annu. Rev. Phytopathol. 9:275–296.

Grant M. R., Godiard L. Sraube E., Ashield T., Leward J., Sattler A., Innes R. W. and Dangl J. L., (1995). Structure of the Arabidopsis RPM1 gene enabling dual specificity disease resistance. Science 269:843–846.

Gyuris J., Golemis E., Chertkov H. and Brent R. (1993). Cdil, a human G1 and S phase protein phosphatase that is associated with Cdk2. Cell 75:791–803.

Keen N. T. (1990). Gene-for-gene complementarity in plant pathogen interactions. Annu. Rev. genet. 24:447–463.

Loh Y. T. and Martin G. B. (1995). The Pto bacterial resistancegene and the Fen insecticide sensitivity gene encode functional protein kinase with serine/threonine specifity. Plant Physiol. 108:1735–1739.

Maeda T., Takekawa M. and Saito H. (1995). Activation of yeast PBS2 MAPKK by MAPKKKs or by binding of an SH3-containing osmosensor. Science 269: 554–558.

Memelink J., Elsevier Trends Journals technical Tips Online, April 2000.

Mes J. J., Weststeijn E. A., Herlaar F., Lambalk J. J. M., Wijbandi J., Haring M. A., and Cornelissen B. J. C., (1999). Biological and molecular characterization of *Fusarium oxysporum* f.sp. *lycopersici* divides race 1 isolates into separate virulence groups. Phytopathology 89:156–160.

Ori N., Eshed Y., I. Paran, G. Presting, D. Aviv, S. tanklsey, D. Zamir, and R. Fluhr (1997) The I-2Cfamily from the wilt disease resistance locus I-2 belongs to the nucleotide binding leucine rich repeat superfamily of plant resistance genes. Plant cell 9: 521–532.

Ramer S. W. and Davis R. W., (1993). A dominant truncation allele identifies a gene, STE20 that encodes a putative protein kinase necessary for mating in *Saccharomyces cerevisiae*. Proc. Natl. Acad. Sci. USA 90: 452–456.

Simons G., Groenendijk J., Wijbrandi J., Reijans M., Groenen J., Diergaarde P., Van der Lee T., Bleeker M., Onstenk J., de Both M., Haring M., Mes J., Cornelissen B., Zabeau M., and Vos P. (1998). Dissection of the *Fusarium* I-2 gene cluster reveals six homologs and one active gene copy. Plant Cell 10:1055–1068.

Strittmatter G., Gheysen G., Gianninazzi-Pearson V., Hahn K., Rohde W., and Tacke E.,(1996). Infections with various types of organisms stimulate transcription from a shorter promoter fragment of the potato GST1 gene. Mol. Plant. Microbe Interact. 9: 68–73.

Song W. Y., Wang G. L., Chen L. L., Kim H. S., Pi L. Y., Holsten T., Gardner J., Wang B., Zhai W. X., Zhu L. H., Fauquet C. and Ronald P. (1995). A receptor kinase like protein encoded by the rice disease resistance gene Xa21. Science 270:1804–1806.

Staskawicz B. J., Ausubel F. M., Baker B. J., Ellis J. G. and Jones J. D. G. (1995). Molecular genetics of plant resistance. Science 268:661–667.

Zhou J., Loh Y. T., Bressan R. A. and Martin G. B. (1995). The tomato gene Pti encodes a serine threonine kinase that is phosphorylated by Pto and is involved in the Hypersensitive Response. Cell 83:925–935.

Zhou J., Tang X. and Martin G. B. (1997). The Pto kinase conferring resistance to tomato bacterial speck disease interacts with proteins that bind a cis-element of pathogenesis related genes. EMBO J. 16:3207–3218.

The invention claimed is:

1. An isolated nucleotide sequence selected from the group consisting of SEQ ID NOs: 1, 3, 5, 7 and 9.

2. The isolated nucleotide sequence according to claim 1, wherein the nucleotide sequence encodes a plant defense signal transduction component.

3. The nucleotide sequence according to claim 1, wherein transduction component is a polypeptide that interacts with the LRR region, the NBS region or the LZ region of a polypeptide encoded by a resistance gene.

4. The nucleotide sequence according to claim 1, wherein the transduction component is a polypeptide that interacts with the N-terminal region or with the C-terminal of a polypeptide encoded by a resistance gene.

5. The nucleotide sequence according to claim 1, wherein the resistance gene is an I-2-resistance gene or a Mi-resistance gene.

6. The nucleotide sequence according to claim 1, wherein the nucleotide sequence encodes an interactor polypeptide selected from the group consisting of SEQ ID NO: 2, 4, 6, 8 and 10.

7. A recombinant vector comprising the nucleotide sequence according to claim 1 under the control of a pathogen inducible.

8. A recombinant vector according to claim 7, wherein the promoter is indicible by a foliar pathogen or by a root pathogen.

9. The recombinant vector according to claim 8 wherein said nucleotide sequence is cloned in an antisense orientation.

10. A cell transformed with the nucleotide sequence according to claim 1.

11. The cell according to claim 10, which is selected from the group consisting of bacteria cells, yeast cells, and plant cells.

12. A plant transformed with the nucleotide sequence according to claim 1.

13. A method regulating the defense response, of a plant against a plant pathogen comprising transforming said plant with the nucleotide sequence according to claim 1.

14. The method according to claim 13, wherein said plant is a dicotyledon or monocotyledon plant species.

15. A method for influencing the defence response of a plant against a plant pathogen comprising transforming the plant with the nucleotide sequence according to claim 2.

16. A method for generating broad resistance in a plant against a plant pathogen comprising transforming the plant with the nucleotide sequence according to claim 3.

17. An isolated nucleotide sequence which encodes a polypeptide selected from the group consisting of SEQ ID NOs. 2, 4, and 10.

18. An isolated nucleotide sequence cormprising SEQ ID NO: 9.

* * * * *